US012239794B2

(12) United States Patent
Hughett, Sr.

(10) Patent No.: US 12,239,794 B2
(45) Date of Patent: *Mar. 4, 2025

(54) URINARY CATHETER KITS

(71) Applicant: C. R. Bard, Inc., Franklin Lakes, NJ (US)

(72) Inventor: James David Hughett, Sr., Monroe, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/593,701

(22) Filed: Mar. 1, 2024

(65) Prior Publication Data

US 2024/0198041 A1    Jun. 20, 2024

Related U.S. Application Data

(63) Continuation of application No. 18/126,879, filed on Mar. 27, 2023, now Pat. No. 11,918,756, which is a
(Continued)

(51) Int. Cl.
  *A61M 25/00* (2006.01)
  *A61M 1/00* (2006.01)
  *A61M 25/10* (2013.01)

(52) U.S. Cl.
  CPC .......... *A61M 25/0017* (2013.01); *A61M 1/84* (2021.05); *A61M 25/002* (2013.01);
(Continued)

(58) Field of Classification Search
  CPC .. A61M 25/0017; A61M 1/84; A61M 25/002; A61M 25/10182;
(Continued)

(56) References Cited

U.S. PATENT DOCUMENTS

| 935,419 A | 9/1909 | Smith |
|---|---|---|
| 2,346,636 A | 4/1944 | Porter |

(Continued)

FOREIGN PATENT DOCUMENTS

| CN | 1511014 A | 7/2004 |
|---|---|---|
| CN | 201823147 U | 5/2011 |

(Continued)

OTHER PUBLICATIONS

U.S. Appl. No. 15/487,297, filed Apr. 13, 2017 Non-Final Office Action dated Apr. 5, 2019.
(Continued)

*Primary Examiner* — Philip R Wiest
*Assistant Examiner* — Brandon W. Levy
(74) *Attorney, Agent, or Firm* — Rutan & Tucker LLP

(57) ABSTRACT

Urinary catheter kits can include a working tray, a storage tray, a protective paperboard, and a urinary catheter assembly, including a urinary catheter and a drainage system. The working tray can be nested on top of the storage tray. The working tray can include preformed sections configured to accommodate a plurality of components of the urinary catheter kit.

20 Claims, 15 Drawing Sheets

Related U.S. Application Data continuation of application No. 17/058,067, filed as application No. PCT/US2019/038051 on Jun. 19, 2019, now Pat. No. 11,612,715.

(60) Provisional application No. 62/724,292, filed on Aug. 29, 2018, provisional application No. 62/687,656, filed on Jun. 20, 2018.

(52) U.S. Cl.
CPC ............... *A61M 25/10182* (2013.11); *A61M 2202/0496* (2013.01); *A61M 2209/06* (2013.01)

(58) Field of Classification Search
CPC ...... A61M 2202/0496; A61M 2209/06; A61M 1/70; A61M 27/00; A61M 2209/08; A61M 2210/1078; A61M 5/002; A61B 50/20; A61B 2050/3006; A61B 2050/3008; A61B 50/33; A61B 50/30; A61B 46/00; A61B 2050/0065; A61B 2050/314; A61B 42/00; A61F 15/001; A61F 13/38

See application file for complete search history.

(56) References Cited

U.S. PATENT DOCUMENTS

| | | |
|---|---|---|
| 2,659,485 A | 11/1953 | Duley et al. |
| 2,874,707 A | 2/1959 | Koppel |
| 2,947,415 A | 8/1960 | Ernest |
| 3,107,786 A | 10/1963 | Adelman |
| 3,137,387 A | 6/1964 | Overment |
| 3,138,253 A | 6/1964 | Harautuneian |
| 3,144,932 A | 8/1964 | Zerbo, Jr. |
| 3,166,189 A | 1/1965 | Disston |
| 3,324,855 A | 6/1967 | Heimlich |
| 3,329,261 A * | 7/1967 | Serany, Jr. ............. A61B 50/30 206/229 |
| 3,345,988 A | 10/1967 | Vitello |
| 3,379,339 A | 4/1968 | Asenbauer |
| 3,485,352 A | 12/1969 | Pilger |
| D218,077 S | 7/1970 | Gabriel |
| 3,542,019 A | 11/1970 | Gittins |
| 3,580,475 A | 5/1971 | Mobley |
| D222,312 S | 10/1971 | Kurtz et al. |
| 3,642,123 A | 2/1972 | Knox |
| 3,650,393 A | 3/1972 | Reiss et al. |
| 3,726,281 A | 4/1973 | Norton et al. |
| 3,762,399 A | 10/1973 | Riedell |
| 3,770,119 A | 11/1973 | Hultberg et al. |
| 3,802,555 A | 4/1974 | Grasty et al. |
| 3,851,649 A * | 12/1974 | Villari .................... A61B 50/30 206/223 |
| D234,404 S | 2/1975 | Merril |
| 3,901,235 A | 8/1975 | Patel et al. |
| D237,315 S | 10/1975 | Nowakowski |
| D237,317 S | 10/1975 | Nowakowski |
| 3,965,900 A | 6/1976 | Boedecker |
| 3,967,728 A | 7/1976 | Gordon et al. |
| 3,976,195 A | 8/1976 | Cohen |
| 3,978,983 A | 9/1976 | Brezette |
| 3,981,398 A | 9/1976 | Boshoff |
| D242,654 S | 12/1976 | Rawls |
| 3,998,221 A | 12/1976 | Collins |
| D243,798 S | 3/1977 | Swartz |
| 4,011,944 A | 3/1977 | Cooley et al. |
| 4,053,280 A | 10/1977 | Salisbury |
| 4,085,845 A | 4/1978 | Perfect |
| D248,871 S | 8/1978 | Forsman et al. |
| D249,362 S | 9/1978 | Forsman et al. |
| 4,116,227 A | 9/1978 | Eisenberg et al. |
| 4,140,127 A | 2/1979 | Cianci et al. |
| 4,149,635 A | 4/1979 | Stevens |
| 4,153,160 A | 5/1979 | Leigh |
| 4,160,505 A | 7/1979 | Rauschenberger |
| 4,170,300 A | 10/1979 | Pick |
| 4,226,328 A | 10/1980 | Beddow |
| 4,256,225 A | 3/1981 | Jackson |
| 4,262,800 A | 4/1981 | Nethercutt |
| 4,266,669 A | 5/1981 | Watson |
| D262,995 S | 2/1982 | Gaba et al. |
| 4,332,322 A | 6/1982 | Jaeschke et al. |
| 4,334,537 A | 6/1982 | Peterson |
| 4,366,901 A | 1/1983 | Short |
| D268,130 S | 3/1983 | Easton |
| 4,458,705 A | 7/1984 | Cawood |
| D275,886 S | 10/1984 | Sheward et al. |
| D276,462 S | 11/1984 | Villarreal |
| D277,508 S | 2/1985 | Clair |
| 4,501,363 A | 2/1985 | Isbey, Jr. |
| 4,522,302 A | 6/1985 | Paikoff |
| 4,523,679 A | 6/1985 | Paikoff et al. |
| 4,530,349 A | 7/1985 | Metzger |
| D280,663 S | 9/1985 | Albon et al. |
| D280,933 S | 10/1985 | McLaughlin |
| D283,051 S | 3/1986 | Fichera |
| 4,595,102 A | 6/1986 | Cianci et al. |
| D287,760 S | 1/1987 | Discko, Jr. |
| 4,767,008 A | 8/1988 | Warnecke et al. |
| 4,795,441 A | 1/1989 | Bhatt |
| 4,811,847 A | 3/1989 | Reif et al. |
| 4,828,113 A | 5/1989 | Friedland et al. |
| 4,844,259 A | 7/1989 | Glowczewskie, Jr. et al. |
| 4,858,821 A | 8/1989 | Bickelhaupt |
| 4,925,448 A | 5/1990 | Bazaral |
| 4,928,830 A | 5/1990 | Brewer |
| 4,944,427 A | 7/1990 | Yamada et al. |
| D310,896 S | 9/1990 | Winjum |
| 4,989,733 A | 2/1991 | Patry |
| 5,007,535 A | 4/1991 | Meseke et al. |
| 5,024,326 A | 6/1991 | Sandel et al. |
| 5,031,768 A | 7/1991 | Fischer |
| 5,098,391 A | 3/1992 | Pantages et al. |
| 5,163,557 A | 11/1992 | Sokolowski |
| 5,170,804 A | 12/1992 | Glassman |
| 5,174,306 A | 12/1992 | Marshall |
| D334,973 S | 4/1993 | Valentine et al. |
| D337,830 S | 7/1993 | Coyne et al. |
| 5,242,398 A | 9/1993 | Knoll et al. |
| D343,687 S | 1/1994 | Houghton et al. |
| 5,306,239 A | 4/1994 | Gurmarnik et al. |
| 5,318,543 A | 6/1994 | Ross et al. |
| 5,322,163 A | 6/1994 | Foos |
| 5,339,955 A | 8/1994 | Horan et al. |
| D351,661 S | 10/1994 | Fischer |
| D353,078 S | 12/1994 | Davis et al. |
| 5,384,103 A | 1/1995 | Miller |
| 5,392,918 A | 2/1995 | Harrison |
| 5,394,983 A | 3/1995 | Latulippe et al. |
| 5,449,071 A | 9/1995 | Levy |
| 5,525,314 A | 6/1996 | Hurson |
| 5,586,163 A | 12/1996 | Goldstein |
| 5,590,778 A | 1/1997 | Dutchik |
| D380,272 S | 6/1997 | Partika et al. |
| D387,177 S | 12/1997 | Davis |
| D387,559 S | 12/1997 | Williamson |
| 5,704,914 A | 1/1998 | Stocking et al. |
| 5,752,234 A | 5/1998 | Withers |
| 5,779,053 A | 7/1998 | Partika et al. |
| 5,810,738 A | 9/1998 | Thomas, II |
| 5,931,303 A | 8/1999 | Salvadori |
| 5,941,241 A | 8/1999 | Weinstein et al. |
| 5,947,284 A | 9/1999 | Foster |
| 5,947,890 A | 9/1999 | Spencer et al. |
| 5,975,295 A | 11/1999 | Diamond |
| 6,004,136 A | 12/1999 | Ehrenpreis |
| 6,012,586 A | 1/2000 | Misra |
| 6,068,121 A | 5/2000 | McGlinch |
| 6,090,075 A | 7/2000 | House |
| 6,121,165 A | 9/2000 | Mackey et al. |
| 6,142,152 A | 11/2000 | Gawarecki |

(56) References Cited

U.S. PATENT DOCUMENTS

| | | | |
|---|---|---|---|
| 6,158,437 A | 12/2000 | Vagley |
| D437,941 S | 2/2001 | Frattini |
| D442,697 S | 5/2001 | Hajianpour |
| D445,198 S | 7/2001 | Frattini |
| D450,130 S | 11/2001 | Goldstein |
| D450,391 S | 11/2001 | Hunt et al. |
| 6,382,212 B1 | 5/2002 | Borchard |
| 6,405,863 B1 | 6/2002 | Dhindsa |
| 6,412,639 B1 | 7/2002 | Hickey |
| 6,454,097 B1 | 9/2002 | Blanco |
| 6,502,699 B1 | 1/2003 | Watson |
| D471,640 S | 3/2003 | McMichael et al. |
| D471,641 S | 3/2003 | McMichael et al. |
| 6,579,271 B1 | 6/2003 | Aruffo et al. |
| D480,816 S | 10/2003 | McMichael et al. |
| 6,640,976 B1 | 11/2003 | Franks-Farah et al. |
| 6,681,933 B1 | 1/2004 | Demsien et al. |
| 6,716,200 B2 | 4/2004 | Bracken et al. |
| 6,769,546 B2 | 8/2004 | Busch |
| D495,491 S | 9/2004 | Ramirez et al. |
| D495,807 S | 9/2004 | Agbodoe et al. |
| 6,793,078 B2 | 9/2004 | Roshdy |
| 6,840,379 B2 | 1/2005 | Franks-Farah et al. |
| 6,896,141 B2 | 5/2005 | McMichael et al. |
| 6,907,992 B2 | 6/2005 | McMichael et al. |
| 6,910,581 B2 | 6/2005 | McMichael et al. |
| 6,915,901 B2 | 7/2005 | Feinberg et al. |
| 6,926,708 B1 | 8/2005 | Franks-Farah et al. |
| 6,948,742 B2 | 9/2005 | Buck |
| 6,959,808 B2 | 11/2005 | Discko, Jr. |
| 6,991,096 B2 | 1/2006 | Gottlieb et al. |
| 7,048,120 B2 | 5/2006 | Pond |
| 7,066,328 B2 | 6/2006 | Pulsifer |
| 7,100,771 B2 | 9/2006 | Massengale et al. |
| D530,920 S | 10/2006 | Snell |
| 7,131,965 B1 | 11/2006 | Thornbury et al. |
| D547,064 S | 7/2007 | Snell |
| D549,454 S | 8/2007 | Åhman |
| 7,264,869 B2 | 9/2007 | Tobita et al. |
| 7,278,987 B2 | 10/2007 | Solazzo |
| D557,047 S | 12/2007 | Dretzka |
| D561,473 S | 2/2008 | Phillips et al. |
| D563,673 S | 3/2008 | Dretzka |
| 7,401,703 B2 | 7/2008 | McMichael et al. |
| 7,410,053 B2 | 8/2008 | Bowen et al. |
| 7,434,687 B2 | 10/2008 | Itou et al. |
| D579,662 S | 11/2008 | Dretzka |
| 7,491,176 B2 | 2/2009 | Mann |
| 7,494,487 B2 | 2/2009 | Timm |
| D590,596 S | 4/2009 | Dretzka |
| D596,311 S | 7/2009 | Antons |
| 7,624,869 B2 | 12/2009 | Primer |
| 7,634,893 B2 | 12/2009 | Gottlieb et al. |
| D609,819 S | 2/2010 | Tomes et al. |
| 7,662,146 B2 | 2/2010 | House |
| D612,153 S | 3/2010 | Liao |
| 7,671,014 B2 | 3/2010 | Beals et al. |
| D613,418 S | 4/2010 | Ryan et al. |
| D618,821 S | 6/2010 | Larsen |
| 7,743,918 B2 | 6/2010 | Itou et al. |
| 7,785,312 B2 | 8/2010 | Thorne, Jr. et al. |
| D623,765 S | 9/2010 | Tomes et al. |
| D631,558 S | 1/2011 | Harmston et al. |
| D636,894 S | 4/2011 | Tomes et al. |
| D638,137 S | 5/2011 | Gross et al. |
| 7,993,326 B2 | 8/2011 | Massengale et al. |
| D646,796 S | 10/2011 | Walter |
| D650,912 S | 12/2011 | Tomes et al. |
| 8,128,595 B2 | 3/2012 | Walker et al. |
| 8,177,064 B2 | 5/2012 | McCormick et al. |
| D662,218 S | 6/2012 | Pittman |
| 8,240,468 B2 | 8/2012 | Wilkinson et al. |
| 8,273,312 B2 | 9/2012 | Porat et al. |
| 8,282,829 B2 | 10/2012 | Yu et al. |
| 8,448,786 B2 | 5/2013 | Tomes et al. |
| D688,461 S | 8/2013 | Ambrefe, Jr. et al. |
| 8,584,849 B2 | 11/2013 | McCaffrey |
| 8,597,505 B2 | 12/2013 | Fulkerson et al. |
| 8,628,549 B2 | 1/2014 | To et al. |
| 8,631,935 B2 | 1/2014 | Tomes et al. |
| 8,656,929 B2 | 2/2014 | Miller et al. |
| 8,662,306 B2 | 3/2014 | Agrawal |
| 8,678,190 B2 | 3/2014 | Tomes et al. |
| 8,708,999 B2 | 4/2014 | Hong et al. |
| D704,856 S | 5/2014 | Tomes et al. |
| D707,848 S | 6/2014 | Shigeno et al. |
| 8,746,452 B2 | 6/2014 | Tomes et al. |
| D708,347 S | 7/2014 | Lober |
| D708,759 S | 7/2014 | Heyman et al. |
| 8,875,940 B2 | 11/2014 | Danchisin et al. |
| D720,470 S | 12/2014 | Lober |
| D720,471 S | 12/2014 | Angel et al. |
| 9,084,593 B2 | 7/2015 | Yakel et al. |
| D738,491 S | 9/2015 | Foley et al. |
| 9,162,781 B2 | 10/2015 | Lien |
| 9,186,217 B2 | 11/2015 | Goyal |
| D751,726 S | 3/2016 | Nishioka et al. |
| 9,283,352 B2 | 3/2016 | Tomes et al. |
| 9,486,604 B2 | 11/2016 | Murray et al. |
| 9,522,001 B2 | 12/2016 | Bui et al. |
| 9,522,753 B2 | 12/2016 | Tomes et al. |
| 9,693,756 B2 | 7/2017 | Tomes et al. |
| 9,744,333 B2 | 8/2017 | Terzibashian |
| 9,745,088 B2 | 8/2017 | Tomes et al. |
| 9,795,761 B2 | 10/2017 | Lockwood et al. |
| 9,808,400 B2 | 11/2017 | Tomes et al. |
| 9,808,596 B2 | 11/2017 | Tomes et al. |
| 9,872,969 B2 | 1/2018 | Conway et al. |
| 10,022,464 B2 | 7/2018 | Sarphati et al. |
| 10,039,897 B2 | 8/2018 | Norris et al. |
| 10,106,295 B2 | 10/2018 | Lockwood |
| 10,251,812 B2 | 4/2019 | Tomes et al. |
| 10,512,752 B2 | 12/2019 | Tomes et al. |
| 10,639,120 B2 | 5/2020 | Turturro et al. |
| 11,490,983 B2 | 11/2022 | Knapp et al. |
| 11,738,171 B2 | 8/2023 | Glithero et al. |
| 2002/0185406 A1 | 12/2002 | Massengale et al. |
| 2003/0038475 A1 | 2/2003 | Stancil |
| 2003/0060761 A1 | 3/2003 | Evans et al. |
| 2003/0075474 A1 | 4/2003 | Moyer et al. |
| 2003/0159966 A1 | 8/2003 | McMichael et al. |
| 2003/0159967 A1 | 8/2003 | McMichael et al. |
| 2003/0159968 A1 | 8/2003 | McMichael et al. |
| 2003/0159969 A1 | 8/2003 | McMichael et al. |
| 2003/0211627 A1 | 11/2003 | Koesterman et al. |
| 2004/0004019 A1 | 1/2004 | Busch |
| 2004/0055919 A1 | 3/2004 | Rowe et al. |
| 2004/0060260 A1 | 4/2004 | Gottlieb et al. |
| 2004/0111072 A1 | 6/2004 | McKissick |
| 2004/0161732 A1 | 8/2004 | Stump et al. |
| 2004/0180822 A1 | 9/2004 | Grafton |
| 2004/0195145 A1 | 10/2004 | Roshdy |
| 2004/0200754 A1 | 10/2004 | Hagemeier |
| 2004/0238391 A1 | 12/2004 | Pond |
| 2005/0022822 A1 | 2/2005 | Santilli et al. |
| 2005/0098470 A1 | 5/2005 | Davis et al. |
| 2005/0101905 A1 | 5/2005 | Merry |
| 2005/0101941 A1 | 5/2005 | Hakky et al. |
| 2005/0236940 A1 | 10/2005 | Rockoff |
| 2005/0256453 A1 | 11/2005 | Nagamatsu |
| 2005/0285385 A1 | 12/2005 | Bova et al. |
| 2006/0009742 A1 | 1/2006 | Solazzo |
| 2006/0086634 A1 | 4/2006 | Steppe |
| 2006/0104857 A1 | 5/2006 | Pigott et al. |
| 2006/0186010 A1 | 8/2006 | Warnack et al. |
| 2006/0205996 A1 | 9/2006 | Presthus et al. |
| 2006/0224086 A1 | 10/2006 | Harty |
| 2006/0264822 A1 | 11/2006 | Nagamatsu |
| 2006/0271019 A1 | 11/2006 | Stoller et al. |
| 2006/0282045 A1 | 12/2006 | Wilkinson et al. |
| 2007/0026472 A1 | 2/2007 | Prokash et al. |
| 2007/0049806 A1 | 3/2007 | Adams et al. |
| 2007/0060908 A1 | 3/2007 | Webster et al. |
| 2007/0084742 A1 | 4/2007 | Miller et al. |

(56) References Cited

U.S. PATENT DOCUMENTS

| | | |
|---|---|---|
| 2007/0088330 A1 | 4/2007 | House |
| 2007/0095699 A1 | 5/2007 | Frieze et al. |
| 2007/0142786 A1 | 6/2007 | Lampropoulos et al. |
| 2007/0156099 A1 | 7/2007 | Fowler |
| 2007/0161971 A1 | 7/2007 | House |
| 2007/0197998 A1 | 8/2007 | Itou et al. |
| 2007/0225687 A1 | 9/2007 | House |
| 2007/0273258 A1 | 11/2007 | Ernst |
| 2007/0299431 A1 | 12/2007 | Jakubowski et al. |
| 2008/0045861 A1 | 2/2008 | Miller et al. |
| 2008/0058725 A1 | 3/2008 | Scribner et al. |
| 2008/0116106 A1 | 5/2008 | Lampropoulos et al. |
| 2008/0121553 A1 | 5/2008 | Gobel |
| 2008/0125722 A1 | 5/2008 | Hess et al. |
| 2008/0172042 A1 | 7/2008 | House |
| 2008/0221515 A1 | 9/2008 | Nagamatsu |
| 2008/0249482 A1 | 10/2008 | Erez |
| 2008/0272023 A1 | 11/2008 | McCormick et al. |
| 2008/0283426 A1 | 11/2008 | Primer et al. |
| 2008/0283433 A1 | 11/2008 | Primer |
| 2009/0026146 A1 | 1/2009 | Carlisle et al. |
| 2009/0076461 A1 | 3/2009 | Susi et al. |
| 2009/0184026 A1 | 7/2009 | Massengale et al. |
| 2009/0194453 A1 | 8/2009 | Thorne, Jr. et al. |
| 2009/0208368 A1 | 8/2009 | Waldrep et al. |
| 2009/0234346 A1 | 9/2009 | McBride, Jr. et al. |
| 2009/0236259 A1 | 9/2009 | Hicks |
| 2010/0274205 A1 | 10/2010 | Morelli et al. |
| 2010/0307941 A1 | 12/2010 | Tomes et al. |
| 2010/0307942 A1 | 12/2010 | Tomes et al. |
| 2010/0311026 A1 | 12/2010 | Tomes et al. |
| 2011/0107494 A1 | 5/2011 | Haines |
| 2011/0120906 A1 | 5/2011 | Umholtz et al. |
| 2011/0155599 A1 | 6/2011 | Yakel et al. |
| 2011/0203957 A1 | 8/2011 | Zoland et al. |
| 2011/0232234 A1 | 9/2011 | Lockwood et al. |
| 2011/0233079 A1 | 9/2011 | Macinnes et al. |
| 2011/0284410 A1 | 11/2011 | Lockwood |
| 2011/0290260 A1 | 12/2011 | Tomes et al. |
| 2011/0290262 A1 | 12/2011 | Tomes et al. |
| 2011/0297147 A1 | 12/2011 | Lick et al. |
| 2012/0145589 A1 | 6/2012 | Macinnes et al. |
| 2012/0150123 A1 | 6/2012 | Lawrence et al. |
| 2012/0222686 A1 | 9/2012 | Lockwood et al. |
| 2012/0262039 A1 | 10/2012 | Daugbjerg et al. |
| 2012/0271161 A1 | 10/2012 | Buckberry |
| 2012/0298114 A1 | 11/2012 | Landsman et al. |
| 2013/0037440 A1 | 2/2013 | Danchisin et al. |
| 2013/0042576 A1 | 2/2013 | Sweeney |
| 2013/0206623 A1 | 8/2013 | Spaargaren et al. |
| 2013/0245496 A1 | 9/2013 | Wells et al. |
| 2013/0269713 A1 | 10/2013 | Bui et al. |
| 2013/0277248 A1 | 10/2013 | Tomes et al. |
| 2013/0277262 A1 | 10/2013 | Nemard |
| 2014/0021087 A1 | 1/2014 | Adler et al. |
| 2014/0039349 A1 | 2/2014 | Moghe et al. |
| 2014/0100551 A1 | 4/2014 | Holmstrom |
| 2014/0142465 A1 | 5/2014 | Tomes et al. |
| 2014/0231287 A1 | 8/2014 | Tomes et al. |
| 2014/0231288 A1 | 8/2014 | Tomes et al. |
| 2014/0262851 A1 | 9/2014 | Adler et al. |
| 2014/0263595 A1 | 9/2014 | Pantelleria |
| 2015/0048103 A1 | 2/2015 | Danchisin et al. |
| 2015/0083627 A1 | 3/2015 | Gorman |
| 2015/0151017 A1 | 6/2015 | Tipton et al. |
| 2015/0258304 A1 | 9/2015 | Tomes et al. |
| 2015/0283354 A1 | 10/2015 | Olson et al. |
| 2015/0335855 A1 | 11/2015 | Tomes et al. |
| 2016/0166800 A1 | 6/2016 | Tomes et al. |
| 2016/0193444 A1 | 7/2016 | Tomes et al. |
| 2016/0228676 A1 | 8/2016 | Glithero et al. |
| 2016/0243332 A1 | 8/2016 | Portela et al. |
| 2017/0056122 A1 | 3/2017 | Ramsey |
| 2017/0056125 A1 | 3/2017 | Garza et al. |
| 2017/0086746 A1 | 3/2017 | Ofek et al. |
| 2017/0106165 A1 | 4/2017 | Holmes |
| 2017/0202699 A1 | 7/2017 | Zani et al. |
| 2017/0216557 A1 | 8/2017 | Kearns et al. |
| 2017/0216558 A1 | 8/2017 | Hughett et al. |
| 2017/0231804 A1 | 8/2017 | Miller et al. |
| 2017/0232226 A1 | 8/2017 | Loui et al. |
| 2017/0296282 A1 | 10/2017 | Turturro et al. |
| 2017/0296283 A1 | 10/2017 | Turturro et al. |
| 2017/0296284 A1 | 10/2017 | Turturro et al. |
| 2017/0319183 A1 | 11/2017 | Tomes et al. |
| 2017/0349305 A1 | 12/2017 | Tomes et al. |
| 2017/0368302 A1 | 12/2017 | Brooks et al. |
| 2018/0001052 A1 | 1/2018 | Lockwood et al. |
| 2018/0056030 A1 | 3/2018 | Tomes et al. |
| 2018/0057196 A1 | 3/2018 | Tomes et al. |
| 2018/0071043 A1 | 3/2018 | Dacey et al. |
| 2018/0206933 A1 | 7/2018 | Healey et al. |
| 2018/0221564 A1 | 8/2018 | Patel et al. |
| 2018/0263655 A1 | 9/2018 | Fjelland et al. |
| 2019/0151195 A1 | 5/2019 | Tomes et al. |
| 2019/0247137 A1 | 8/2019 | Gallagher |
| 2020/0353204 A1 | 11/2020 | Glithero et al. |
| 2020/0360103 A1 | 11/2020 | Knapp et al. |
| 2020/0383743 A1 | 12/2020 | Howell et al. |
| 2021/0100978 A1 | 4/2021 | Gohde |
| 2021/0196922 A1 | 7/2021 | Hughett, Sr. |
| 2023/0226310 A1 | 7/2023 | Hughett, Sr. |
| 2023/0310795 A1 | 10/2023 | Hughett, Sr. |
| 2023/0390522 A1 | 12/2023 | Glithero et al. |
| 2024/0108857 A1 | 4/2024 | Gohde |
| 2024/0225771 A1 | 7/2024 | Knapp et al. |
| 2024/0226502 A1 | 7/2024 | Chapman |
| 2024/0269427 A1 | 8/2024 | Legaspi et al. |

FOREIGN PATENT DOCUMENTS

| | | |
|---|---|---|
| DE | 2339724 A1 | 2/1975 |
| DE | 102007003223 B4 | 12/2009 |
| EP | 1595561 A2 | 11/2005 |
| EP | 1731189 A1 | 12/2006 |
| FR | 2780274 A1 | 12/1999 |
| FR | 2873929 A1 | 2/2006 |
| GB | 2365342 A | 2/2002 |
| JP | S50149175 A | 11/1975 |
| JP | 2002136597 A | 5/2002 |
| JP | 2005506110 A | 3/2005 |
| JP | 2007229520 A | 9/2007 |
| JP | 2007319535 A | 12/2007 |
| JP | 2010200809 A | 9/2010 |
| JP | 2011520578 A | 7/2011 |
| WO | 9106255 A1 | 5/1991 |
| WO | 9607364 A1 | 3/1996 |
| WO | 02004942 A1 | 1/2002 |
| WO | 02064078 A1 | 8/2002 |
| WO | 2002083021 A1 | 10/2002 |
| WO | 2004005157 A1 | 1/2004 |
| WO | 2005027767 A1 | 3/2005 |
| WO | 2006114466 A1 | 11/2006 |
| WO | 2007045943 A1 | 4/2007 |
| WO | 2008033873 A2 | 3/2008 |
| WO | 2008139852 A1 | 11/2008 |
| WO | 2015057999 | 4/2015 |
| WO | 2017147067 A1 | 8/2017 |
| WO | 2018044772 A1 | 3/2018 |
| WO | 2018057835 A1 | 3/2018 |
| WO | 2018183752 A1 | 10/2018 |
| WO | 2018190865 A1 | 10/2018 |
| WO | 2019209867 A1 | 10/2019 |
| WO | 2019246307 A1 | 12/2019 |
| WO | 2020235995 A1 | 11/2020 |
| WO | 2021081434 A1 | 4/2021 |
| WO | 2022250994 A1 | 12/2022 |
| WO | 2022265999 A1 | 12/2022 |

OTHER PUBLICATIONS

U.S. Appl. No. 15/487,297, filed Apr. 13, 2017 Notice of Allowance dated Oct. 2, 2020.

(56) References Cited

OTHER PUBLICATIONS

U.S. Appl. No. 15/487,297, filed Apr. 13, 2017 Restriction Requirement dated Jun. 11, 2020.
U.S. Appl. No. 15/487,297, filed Apr. 13, 2017 Restriction Requirement dated Nov. 29, 2018.
U.S. Appl. No. 16/497,770, filed Sep. 25, 2019 Advisory Action dated Dec. 12, 2022.
U.S. Appl. No. 16/497,770, filed Sep. 25, 2019 Advisory Action dated Jul. 27, 2023.
U.S. Appl. No. 16/497,770, filed Sep. 25, 2019 Final Office Action dated Jun. 7, 2023.
U.S. Appl. No. 16/497,770, filed Sep. 25, 2019 Final Office Action dated Sep. 23, 2022.
U.S. Appl. No. 16/497,770, filed Sep. 25, 2019 Non-Final Action dated Jan. 13, 2023.
U.S. Appl. No. 16/497,770, filed Sep. 25, 2019 Non-Final Office Action dated Jun. 1, 2022.
U.S. Appl. No. 16/497,770, filed Sep. 25, 2019 Notice of Allowance dated Sep. 22, 2023.
U.S. Appl. No. 16/639,059, filed Feb. 13, 2020 Non-Final Office Action dated Feb. 8, 2022.
U.S. Appl. No. 16/639,059, filed Feb. 13, 2020 Notice of Allowance dated Jul. 1, 2022.
U.S. Appl. No. 16/639,059, filed Feb. 13, 2020 Restriction Requirement dated Oct. 13, 2021.
U.S. Appl. No. 16/943,902, filed Jul. 30, 2020 Notice of Allowance dated Apr. 5, 2023.
U.S. Appl. No. 16/943,902, filed Jul. 30, 2020 Restriction Requirement dated Nov. 1, 2022.
U.S. Appl. No. 17/058,067, filed Nov. 23, 2020 Non-Final Office Action dated Jul. 7, 2022.
U.S. Appl. No. 17/058,067, filed Nov. 23, 2020 Notice of Allowance dated Nov. 23, 2022.
U.S. Appl. No. 17/982,288, filed Nov. 7, 2022 Advisory Action dated Jul. 28, 2023.
U.S. Appl. No. 17/982,288, filed Nov. 7, 2022 Final Office Action dated Jun. 9, 2023.
U.S. Appl. No. 17/982,288, filed Nov. 7, 2022 Non-Final Office Action dated Aug. 28, 2023.
U.S. Appl. No. 17/982,288, filed Nov. 7, 2022 Non-Final Office Action dated Feb. 22, 2023.
U.S. Appl. No. 17/982,288, filed Nov. 7, 2022 Notice of Allowance dated Nov. 15, 2023.
U.S. Appl. No. 18/126,879, filed Mar. 27, 2023 Notice of Allowance dated Nov. 2, 2023.
U.S. Appl. No. 18/207,075, filed Jun. 7, 2023 Notice of Allowance dated Aug. 11, 2023.
U.S. Appl. No. 18/236,331, filed Aug. 21, 2023 Non-Final Office Action dated Mar. 5, 2024.
"Arrow International, Inc. Introduces Maximal Barrier Precautions Tray", Press release. Jan. 11, 2006.
"Uniting the best of Healthcare" http://ghx.com/about/, last accessed 2019.
Addison, R. et al., "Catheter Care," Royal College of Nursing, London (2008).
American Journal of Infection Control. vol. 46 (2018) SI6-67.
Arrow, "Arrow Trauma Products" brochure, 2000.
AU 2014337176 filed Mar. 15, 2016 Examination Report dated Aug. 1, 2018.
Bardex I.C. Complete Care StateLock Device 350 ml Urine Meter Foley Tray with Bacteriostatic Collection System, Directions for Use; Dated 2006.
Bardex I.C. Infection Control 350 ml Urine Meter Foley Tray, Directions for Use; Dated 2006.
Bardex I.C. Infection Control Foley Tray, Directions for Use; Dated 2006.
C. R. Bard Urological Drainage, https://www.crbard.com/medical/Professionals/Product-Concentrations/Urological-Drainage, last accessed 2019.
C.R. Bard, Inc; "A few important words about Catheter Care"; Dated 2001.
California Department of Public Health, "Catheter-Associated Urinary Tract Infection (CAUTI) Prevention" (2015).
CN 201480057141.5 filed Apr. 18, 2016 Office Action dated Dec. 4, 2018.
Dept. of Health and Human Services, "Action Plan to Prevent Healthcare-Associated Infections." (2009).
Dobkin et al., "Myth and Measurement—The Case of Medical Bankruptcies," 378 New Eng. J. Med., 1076-78 (2018).
Ellen Elpern, et al., "Prevention of Catheter-Associated Urinary Tract Infections in Adults," 36 Critical Care Nurse, 9 (2016).
EP 14853869.7 filed Mar. 31, 2016 Extended European Search Report dated Aug. 4, 2017.
EP 14853869.7 filed Mar. 31, 2016 Office Action dated Mar. 13, 2019.
Foxman, B. "Epidemiology of Urinary Tract Infections: Incidence, Morbidity, and Economic Costs." The American Journal of Medicine, 113 Suppl 1A (2002).
Gould et al., "Catheter-associated Urinary Tract Infection (CAUTI) Toolkit," Centers for Disease Control and Prevention Devision of Healthcare Quality Promotion. (2009).
Gould et al., "Guideline For Prevention Of Catheter Associated Urinary Tract Infections," Centers for Disease Control Healthcare Infection Control Practices Advisory Committee, (2009).
Greene, L. et al. "Guide to the Elimination of Catheter-Associated Urinary TractInfections (CAUTIs): Developing and Applying Facility-Based Prevention Interventions in Acute and Long-Term Care Settings," Association for Professionals in Infection Control and Epidemiology, (2008).
Jacobsen, S.M. et al., "Complicated Catheter-Associated UrinaryTract Infections Due to *Escherichia coli* and Proteus mirabilis", 21 Clinical Microbiology Reviews 1, 26-59 (Jan. 2008).
Jennifer A Meddings, "Implementing Strategies to Reduce Hospital-Acquired Catheter-Associated Urinary Tract Infection," Wound, Ostomy and Continence Nurses Society, www.catheterout.org, (Jun. 2010).
JP 2016-523921 filed Apr. 15, 2016 Office Action dated Jul. 11, 2018.
Linda Kohn et al., eds., "To Err is Human: Building a Safer Health System," Institute of Medicine (US), (2000).
Lo, E. et al., "Strategies to Prevent Catheter-Associated Urinary Tract Infections in Acute Care Hospitals," Infection Control and Hospital Epidemiology. 29, S41-S50 (2008).
Madeo M. et al., "Reducing the risks associated with urinary catheters." Nursing Standard, vol. 23, No. 29, 47-55 (2009).
Male Catheter Insertion Video, Uploaded to YouTube on Feb. 7, 2008, Parts 1 and 2. https://www.youtube.com/watch?v=ISBAya_5clM (Last accessed Feb. 26, 2020).
Norman, Donald A., The Design of Everyday Things, 2002 ed. (Excerpt).
Ortega, R. et al. "Female Urethral Catheterization", N Engl J Med 2008; 358: e15. Apr. 3, 2008.
PCT/US14/60963 filed Oct. 16, 2014 International Search Report and Written Opinion dated Jan. 14, 2015.
PCT/US20/35371 filed May 29, 2020 International Search Report and Written Opinion dated Sep. 14, 2020.
PCT/US2017/027628 filed Apr. 14, 2017 International Search Report and Written Opinion dated Jul. 17, 2017.
PCT/US2018/025260 filed Mar. 29, 2018 International Search Report and Written Opinion dated Jun. 7, 2018.
PCT/US2019/038051 filed Jun. 19, 2019 International Prelliminary Report on Patentability dated Dec. 22, 2020.
PCT/US2019/038051 filed Jun. 19, 2019 International Search Report and Written Opinion dated Aug. 29, 2019.
PCT/US2022/029394 filed May 16, 2022 International Search Report and Written Opinion dated Sep. 21, 2022.
PCT/US2022/033271 filed Jun. 13, 2022 International Search Report and Written Opinion dated Oct. 13, 2022.
Raheem, "Application of Plastics and Paper as Food Packaging Materials" An Overview, 2017, Emirates Journal of Food and Agriculture, vol. 25, pp. 177-188 (Year: 2017).

(56) References Cited

OTHER PUBLICATIONS

Request for Inter partes Review of U.S. Pat. No. 8,631,935, filed Dec. 30, 2014.
Saint et al., "Catheter-Associated Urinary Tract Infection and the Medicare Rule Changes," Annals of Internal Medicine, Jun. 16, 2009.
Steultjens, M.P.M. et al., "Range of joint motion and disability in patients with osteoarthritis of the knee or hip," Rheumatology, Bristish Society for Rheumatology. (2000).
The Joint Commision on National Patient Safety, "2012 National Patient Safety Goals: Hospital accreditation Program." (2012).
Thomson et al. "Male Urethral Catheterization", N Engl J Med 2006; 354: e22. May 25, 2006.
Urological Drainage website, http://m.bardmedical.com/products/urological-drainage/, last accessed 2019.
U.S. Appl. No. 15/029,613, filed Apr. 14, 2016 Final Office Action dated Apr. 10, 2019.
U.S. Appl. No. 15/029,613, filed Apr. 14, 2016 Non-Final Office Action dated Nov. 29, 2018.
U.S. Appl. No. 15/487,297, filed Apr. 13, 2017 Advisory Action dated Apr. 28, 2020.
U.S. Appl. No. 15/487,297, filed Apr. 13, 2017 Final Office Action dated Feb. 21, 2020.
EP 24176270.7 filed May 16, 2024 Extended European Search Report dated Sep. 26, 2024.
PCT/US2019/028784 filed Nov. 23, 2020 Extended European Search Report dated May 31, 2021.
U.S. Appl. No. 18/236,331, filed Aug. 21, 2023 Notice of Allowance dated Aug. 7, 2024.
U.S. Appl. No. 18/536,972, filed Dec. 12, 2023 Non-Final Office Action dated Jul. 19, 2024.
U.S. Appl. No. 18/615,657, filed Mar. 25, 2024 Non-Final Office Action dated Oct. 4, 2024.

\* cited by examiner

URINARY CATHETER KITS

PRIORITY

This application is a continuation of U.S. patent application Ser. No. 18/126,879, filed Mar. 27, 2023, now U.S. Pat. No. 11,918,756, which is a continuation of U.S. patent application Ser. No. 17/058,067, filed Nov. 23, 2020, now U.S. Pat. No. 11,612,715, which is a U.S. national stage of International Application No. PCT/US2019/038051, filed Jun. 19, 2019, which claims the benefit of priority to U.S. Provisional Application No. 62/687,656, filed Jun. 20, 2018, and to U.S. Provisional Application No. 62/724,292, filed Aug. 29, 2018, each of which is incorporated by reference in its entirety into this application.

BACKGROUND

Urinary catheters are used in healthcare facilities such as hospitals to drain urine from patients. However, the second most common form of hospital-acquired infection ("HAI") is catheter-associated urinary tract infection ("CAUTI"). As such, hospitals are interested in ways to cut their CAUTI rates by conforming to strict aseptic techniques as part of their standard of care. But there are many factors that influence a hospital's ability to meet that standard of care. These factors include aspects of healthcare-practitioner training and experience, patient factors (e.g., general health, weight, and anatomy), environmental factors, and characteristics of urinary catheter-insertion kits including components of the kits, various layouts of the components in the kits, and instructions for use of such kits. There is a need in healthcare for an easy, safe, and reliable standard method for inserting a catheter into a patient. Disclosed herein are catheter-insertion kits, including urinary catheter insertion kits, with integrated instructions for use and methods thereof that address the foregoing.

SUMMARY

Disclosed herein is urinary catheter-insertion kit including, in some embodiments, a working tray, a storage tray, a catheter (by way of non-limiting example, a fluid drainage catheter, such as a urinary catheter), and a drainage system including drainage tubing and a drainage receptacle. The working tray is configured to nest with the storage tray by suspending the working tray from the storage tray. According to some embodiments, the working tray is fixed to the storage tray to at least substantially prevent their separation. At least the working tray includes a number of preformed sections configured to hold a number of components of the urinary catheter-insertion kit. At least one section of the preformed sections of the working tray includes a catheter section configured to hold the catheter. The storage tray is configured to hold the drainage system.

In some embodiments, suspending the working tray from the storage tray includes inserting folded-over longitudinal edges or tabs of a paperboard storage tray in a gap between longitudinal sides and an overhang of the working tray. The gap includes a number of protrusions configured to engage the folded-over longitudinal edges or tabs of the paperboard storage tray and fasten together the working tray and the storage tray.

In some embodiments, the storage tray includes a cutout in an end of the storage tray. The cutout in the end of the storage tray is configured to facilitate access to any of the components of the urinary catheter-insertion kit stored in the storage tray while working from the working tray.

In some embodiments, the working tray includes a cutout in a corner area of the catheter section formed between a bottom portion and an end portion of the catheter section. The cutout in the corner area of the catheter section is configured to allow the drainage tubing to pass from the storage tray to the working tray by way of a bottom of the cutout when the drainage tubing is stored in the storage tray. According to other embodiments, there is no cut-out but instead the working tray edge nearest the cut-out end of the storage tray is short enough to permit the drainage tubing to extend from the storage tray to the working tray.

In some embodiments, a side of the cutout in the corner area of the catheter section is configured to allow the drainage tubing to be removed from the storage tray without disconnecting the drainage tubing from the catheter when the drainage tubing and the catheter are pre-connected in the urinary catheter-insertion kit.

In some embodiments, the working tray includes a drainage-tubing constriction between the cutout in the corner area of the catheter section and a remainder of the catheter section. The drainage-tubing constriction is configured to hold a portion of the drainage tubing and maintain an initial placement of the urinary catheter in the working tray until the urinary catheter is used.

In some embodiments, the urinary catheter-insertion kit further includes a connector configured to connect the catheter to the drainage tubing. The connector is pre-connected to at least the catheter in the urinary catheter-insertion kit. The connector includes a urine-sampling port.

In some embodiments, the urinary catheter-insertion kit further includes a lubricant container including lubricant for the catheter. At least one section of the preformed sections of the working tray includes a lubricant-container section configured to hold the lubricant container.

In some embodiments, the urinary catheter-insertion kit further includes an inflatant container including an inflatant for inflating a balloon of the catheter. At least one section of the preformed sections of the working tray includes an inflatant-container section configured to hold the inflatant container.

In some embodiments, the urinary catheter-insertion kit further includes a genital-preparation kit including a package of an antiseptic and one or more swab sticks. At least one section of the preformed sections of the working tray includes a genital-preparation section configured with a well to hold the antiseptic from the package. The genital-preparation section also includes one or more angled channels to respectively hold the one or more swab sticks with their corresponding one or more absorbent heads in the well.

In some embodiments, the well is dimensioned to have a volume commensurate with an entire volume of the antiseptic from the package plus a volume of the one or more absorbent heads such that the one or more absorbent heads become saturated with the antiseptic when the antiseptic from the package is dispensed in the well.

In some embodiments, the urinary catheter-insertion kit further includes a urine-sampling container. At least one section of the preformed sections of the working tray includes a urine sampling-container section configured to hold the urine-sampling container. Alternatively, the storage tray is configured to hold the urine-sampling container instead of the working tray.

In some embodiments, the urinary catheter-insertion kit further includes step-by-step catheterization instructions imprinted directly on at least the working tray.

In some embodiments, the urinary catheter-insertion kit further includes an instruction to not separate the working tray from the storage tray along with the step-by-step catheterization instructions imprinted directly on at least the working tray.

In some embodiments, the urinary catheter-insertion kit further includes protective paperboard configured to protect at least the components of the working tray. The working tray includes a lip around a perimeter of the working tray configured to hold the paperboard.

In some embodiments, the urinary catheter-insertion kit further includes a peri-care kit. The urinary catheter-insertion kit is configured to include the peri-care kit between the paperboard and an outer packaging of the urinary catheter-insertion kit.

Also disclosed herein is urinary catheter-insertion kit including, in some embodiments, a working tray including a Foley catheter, a lubricant-filled syringe for lubricating the catheter, a saline-filled syringe for inflating a balloon of the catheter, a genital-preparation kit including a package of an antiseptic and one or more swab sticks, and a urine-sampling container; a storage tray including a drainage system including drainage tubing and a drainage receptacle; and step-by-step catheterization instructions imprinted directly on at least the working tray. At least the working tray includes a number of preformed sections holding a number of components of the urinary catheter-insertion kit. At least one section of the preformed sections of the working tray includes a catheter section including the catheter, a lubricant-syringe section including the lubricant-filled syringe, a saline-syringe section including the saline-filled syringe, and a genital-preparation section including the package of the antiseptic and the one or more swab sticks. At least one section of the preformed sections of the working tray includes a urine sampling-container section including the urine-sampling container. Alternatively, the storage tray is configured to hold the urine-sampling container instead of the working tray. The genital-preparation section is configured with a well to hold the antiseptic from the package. The genital-preparation section also includes one or more angled channels holding the one or more swab sticks with their absorbent heads in the well. The working tray is configured to nest with the storage tray by suspending the working tray from the storage tray. The working tray includes a cutout in a corner area of the catheter section formed between a bottom portion and an end portion of the catheter section. The drainage system is pre-connected to the catheter through a connector having a urine-sampling port. The cutout in the corner area of the catheter section is configured to allow the drainage tubing to pass from the storage tray where the drainage system is stored to the working tray by way of a bottom of the cutout in the corner area of the catheter section.

In some embodiments, the working tray includes a drainage-tubing constriction between the cutout in the corner area of the catheter section and a remainder of the catheter section. The drainage-tubing constriction is configured to hold a portion of the drainage tubing and maintain an initial placement of the urinary catheter in the working tray until the urinary catheter is used.

Also disclosed herein is a method of urinary catheterization with a urinary catheter-insertion kit including, in some embodiments, removing an outer packaging from the urinary catheter-insertion kit, cleaning a patient's perianal area with a peri-care kit, preparing the patient's genital area using a genital-preparation kit, and catheterizing the patient with a Foley catheter. Removing the outer packaging from the urinary catheter-insertion kit bares a working tray suspendedly nested with a storage tray with step-by-step catheterization instructions imprinted directly on at least the working tray. The working tray includes a number of preformed sections holding a number of components for the method of urinary catheterization with the urinary catheter-insertion kit. Removing the outer packaging from the urinary catheter-insertion kit also bares a protective paperboard configured to protect the components of the urinary catheter-insertion kit in the working tray under the paperboard. Cleaning the patient's perianal area with the peri-care kit includes removing the peri-care kit from between the outer packaging of the urinary catheter-insertion kit and the paperboard over the working tray. Preparing the patient's genital area using the genital-preparation kit includes using a package of an antiseptic and one or more swab sticks of the genital-preparation kit. Preparing the patient's genital area includes removing the package of the antiseptic from a genital-preparation section of the working tray and dispensing the antiseptic into a well of the genital-preparation section, thereby saturating one or more absorbent heads of one or more corresponding swab sticks respectively held in one or more angled channels of the genital-preparation section. Catheterizing the patient with the catheter includes removing the catheter from a catheter section of the working tray and a drainage system from the storage tray without disconnecting the catheter from either drainage tubing or a drainage receptacle of the drainage system.

In some embodiments, the working tray includes a cutout in a corner area of the catheter section formed between a bottom portion and an end portion of the catheter section. The cutout enables removing both the catheter from the catheter section of the working tray and the drainage system from the storage tray without disconnecting the catheter from the drainage system.

In some embodiments, the method further includes removing the drainage tubing from a drainage-tubing constriction in the working tray between the cutout in the corner area of the catheter section and a remainder of the catheter section.

In some embodiments, dispensing the antiseptic into the well of the genital-preparation section of the working tray is in accordance with the step-by-step catheterization instructions imprinted directly on the working tray.

In some embodiments, preparing the patient's genital area includes retracting the patient's genitals using a non-dominant hand and swabbing the patient's genitals with the antiseptic using a dominant hand in accordance with the step-by-step catheterization instructions imprinted directly on the working tray.

In some embodiments, the method further includes removing a lubricant-filled syringe from a lubricant-syringe section of the working tray, dispensing the lubricant from the lubricant-filled syringe into the catheter section of the working tray, and lubricating the catheter with the lubricant dispensed in the lubricant-syringe section of the working tray. At least dispensing the lubricant into the catheter section and lubricating the catheter with the lubricant dispensed in the catheter section of the working tray are in accordance with the step-by-step catheterization instructions imprinted directly on the working tray.

In some embodiments, the method further includes removing a saline-filled syringe from a saline-syringe section of the working tray and attaching the saline-filled syringe to the catheter for inflating a balloon of the catheter. At least attaching the saline-filled syringe to the catheter is in accordance with the step-by-step catheterization instructions imprinted directly on the working tray.

In some embodiments, catheterizing the patient includes inserting the catheter into the patient's urethra and inflating the balloon with saline from the saline-filled syringe. At least inflating the balloon with saline from the saline-filled syringe is in accordance with the step-by-step catheterization instructions imprinted directly on the working tray.

These and other features of the concepts provided herein will become more apparent to those of skill in the art in view of the accompanying drawings and following description, which disclose particular embodiments of such concepts in greater detail.

DESCRIPTION

Figure 1A:
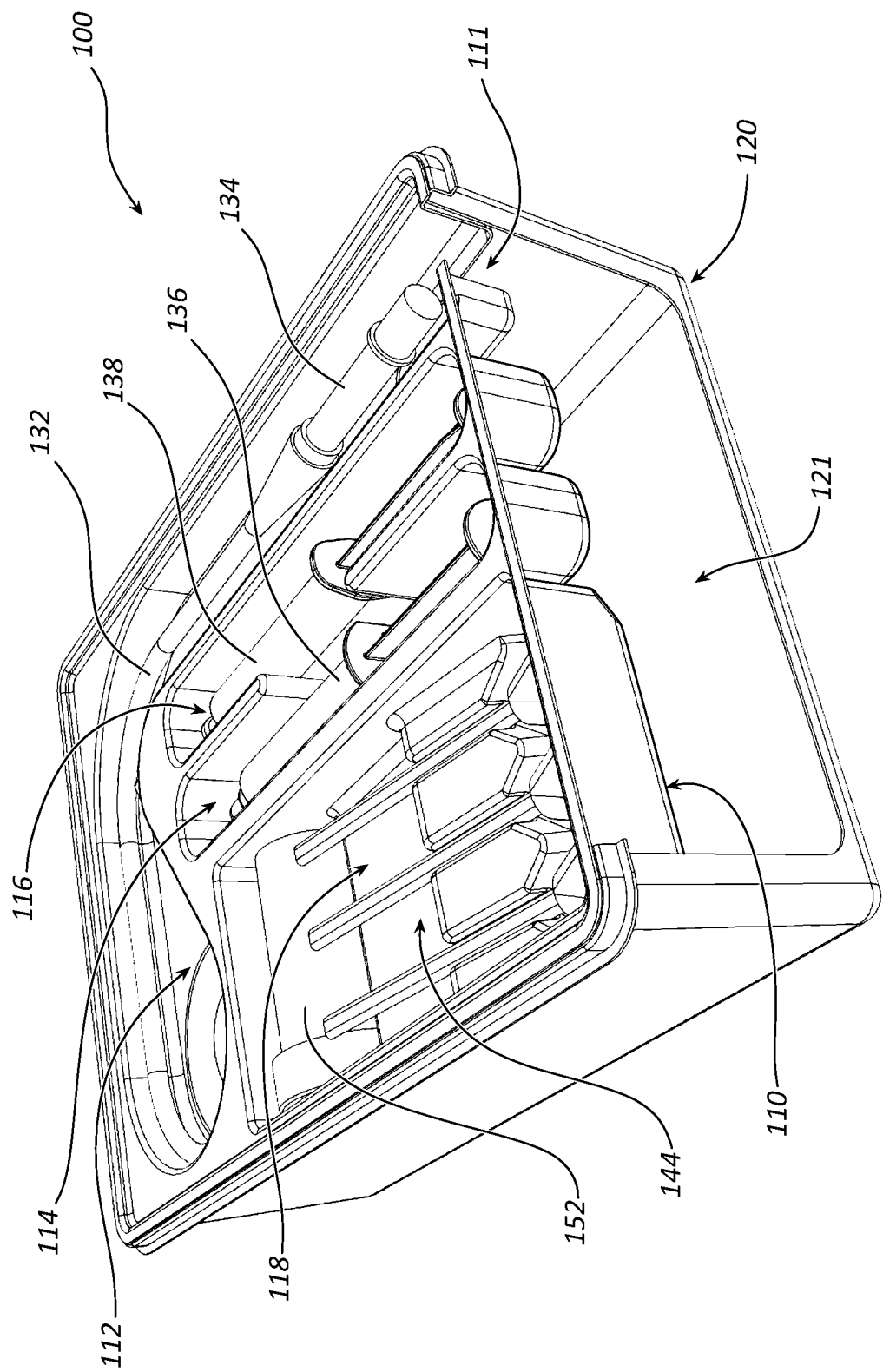
FIG. 1A provides a perspective view of a urinary catheter-insertion kit including at least some components in a working tray of the urinary catheter-insertion kit in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

Urinary catheters are used in healthcare facilities such as hospitals to drain urine from patients. However, the second most common form of hospital-acquired infection ("HAI") is catheter-associated urinary tract infection ("CAUTI"). As such, hospitals are interested in ways to cut their CAUTI rates by conforming to strict aseptic techniques as part of their standard of care. But there are many factors that influence a hospital's ability to meet that standard of care. These factors include aspects of healthcare-practitioner training and experience, patient factors (e.g., general health, weight, and anatomy), environmental factors, and characteristics of urinary catheter-insertion kits including components of the kits, various layouts of the components in the kits, and instructions for use of such kits. There is a need in healthcare for an easy, safe, and reliable standard method for inserting a urinary catheter into a patient. Disclosed herein are urinary catheter-insertion kits with integrated instructions for use and methods thereof that provide an easy, safe, and reliable standard method for inserting a urinary catheter into a patient, thereby reducing CAUTI rates.

Urinary Catheter-Insertion Kits

Figure 1B:
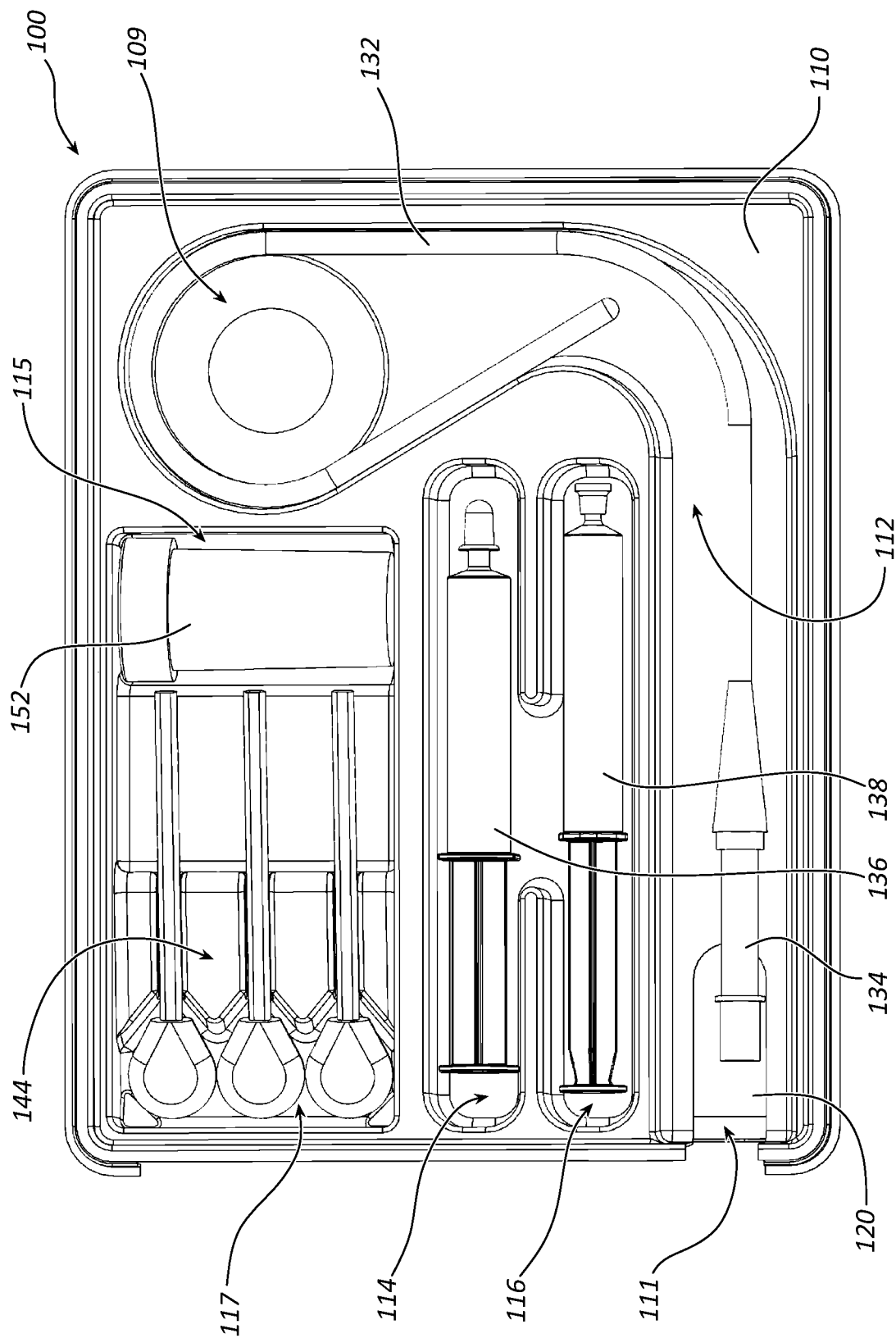
FIG. 1B provides a top view of the urinary catheter-insertion kit of FIG. 1A.
Figure 1C:
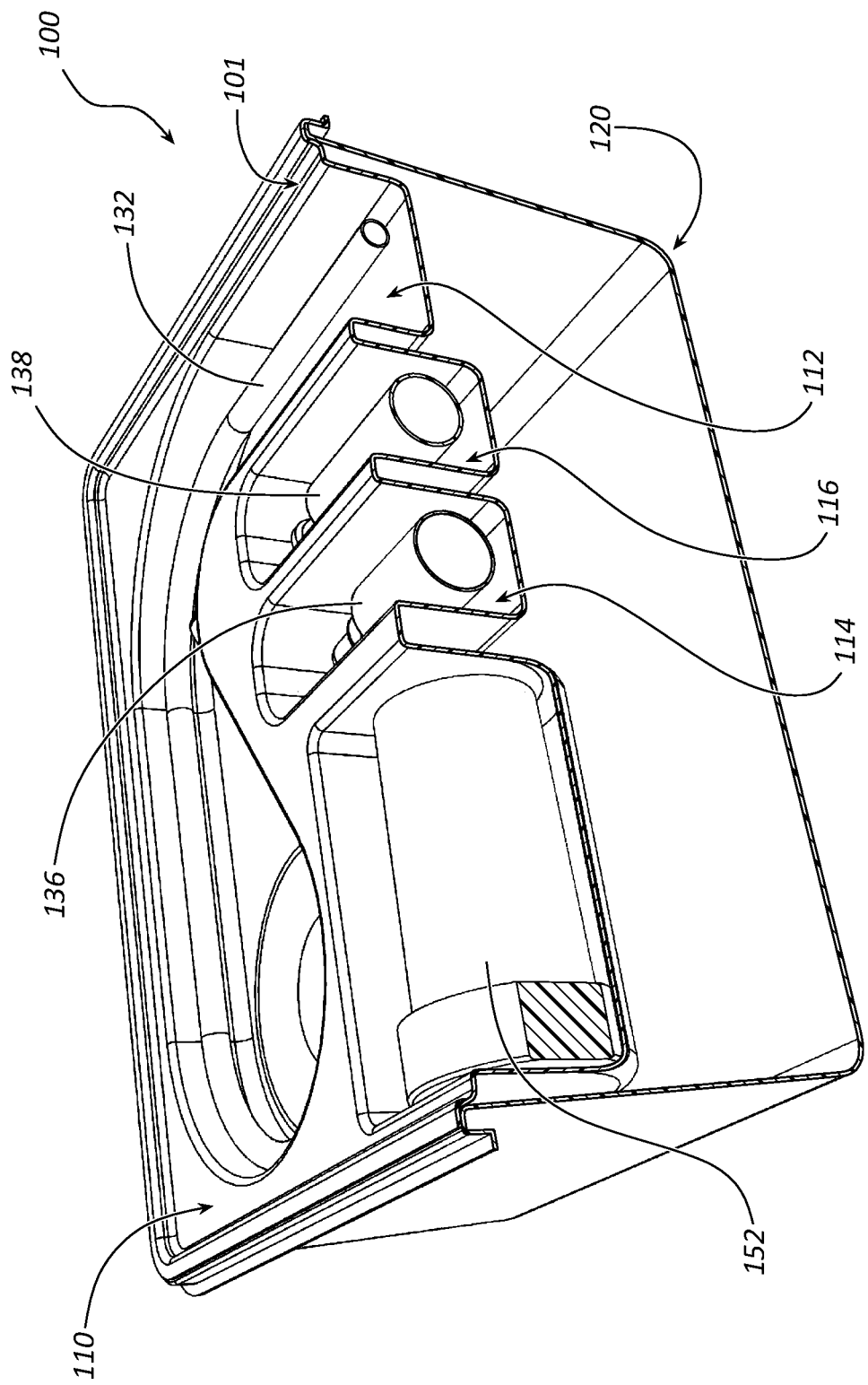
FIG. 1C provides a first cross-sectional view of the urinary catheter-insertion kit of FIG. 1A.
Figure 1D:
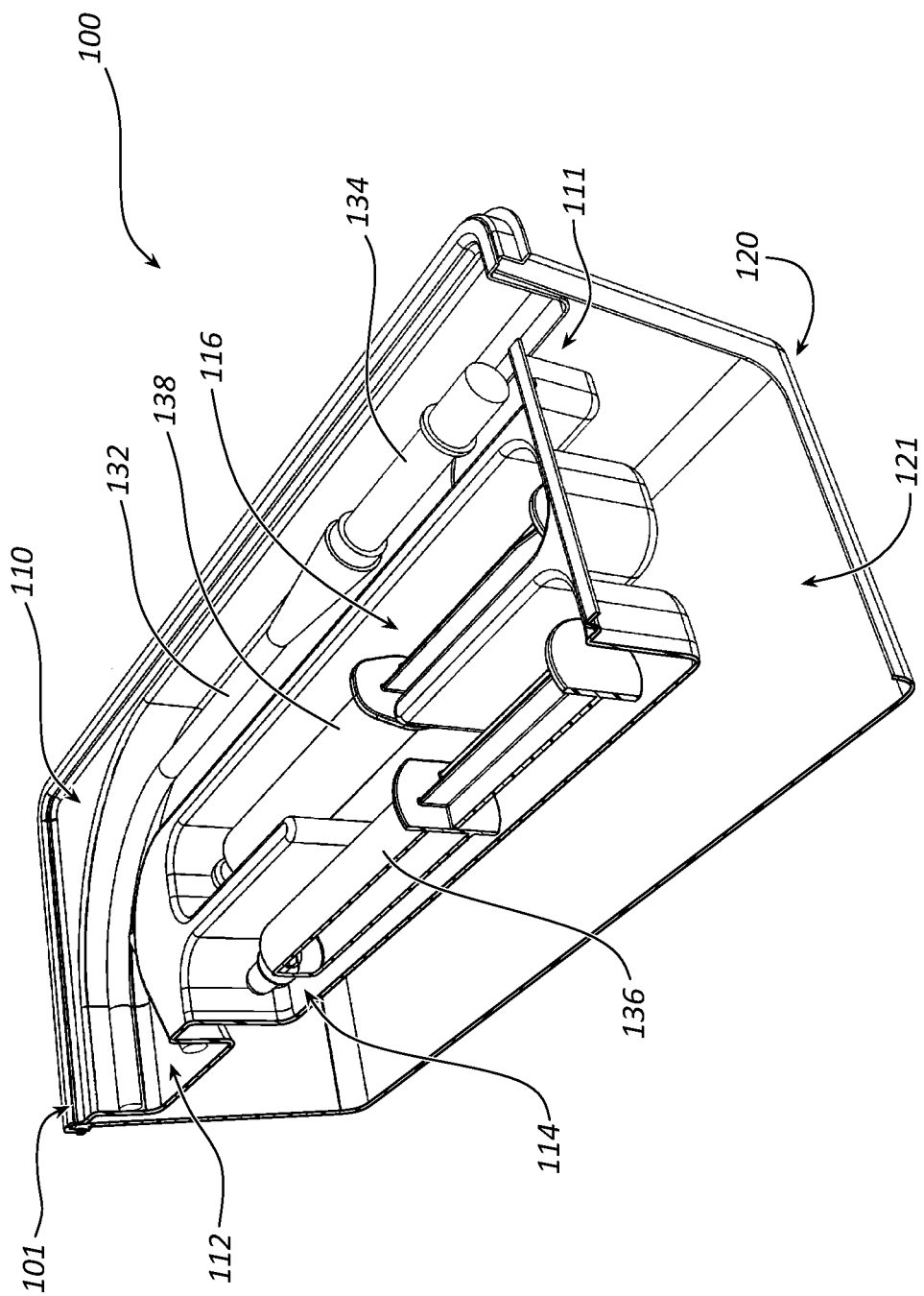
FIG. 1D provides a second cross-sectional view of the urinary catheter-insertion kit of FIG. 1A.
Figure 2A:
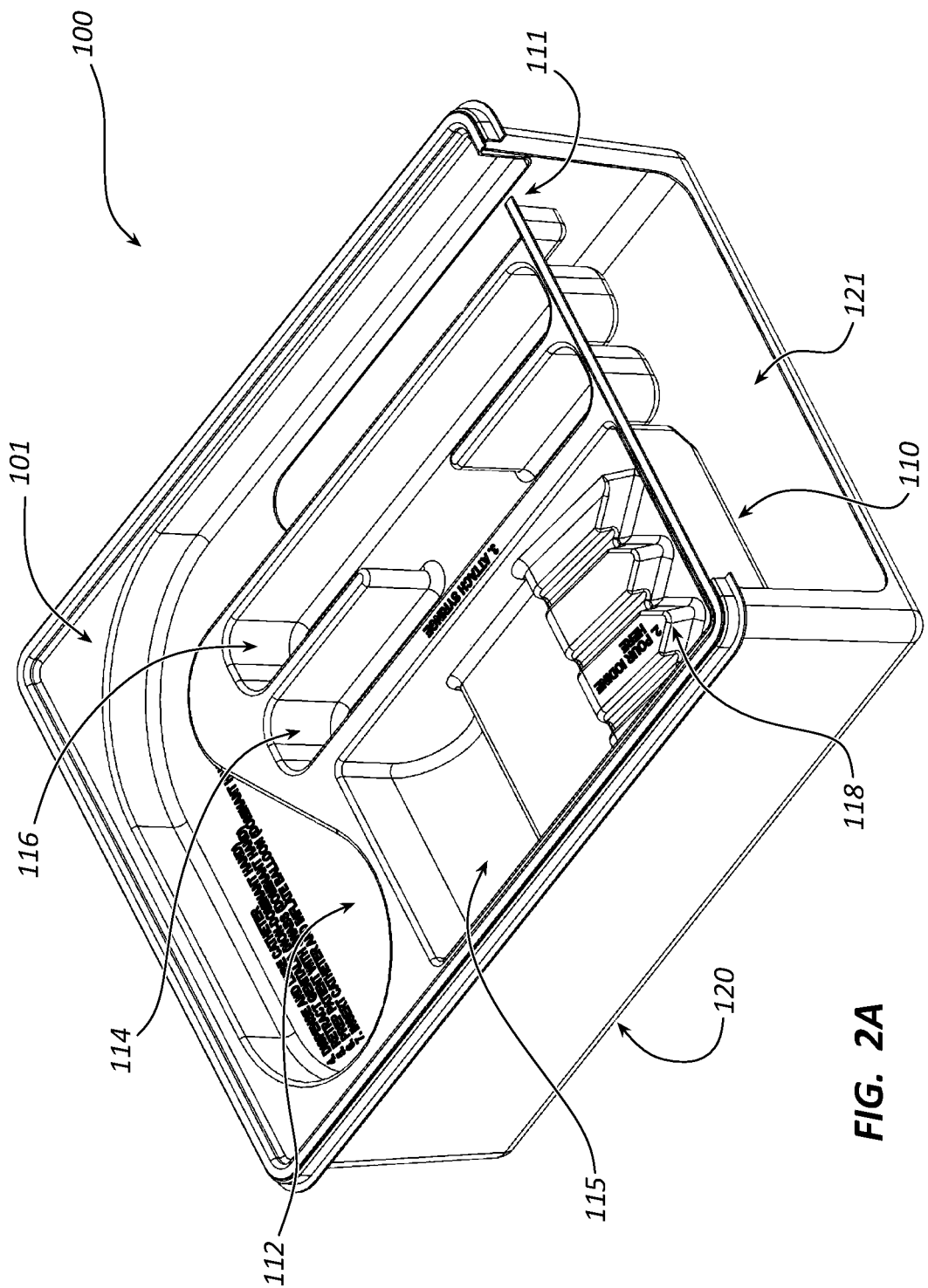
FIG. 2A provides a perspective view of alternative nested trays of a urinary catheter-insertion kit in accordance with some embodiments.
Figure 2B:
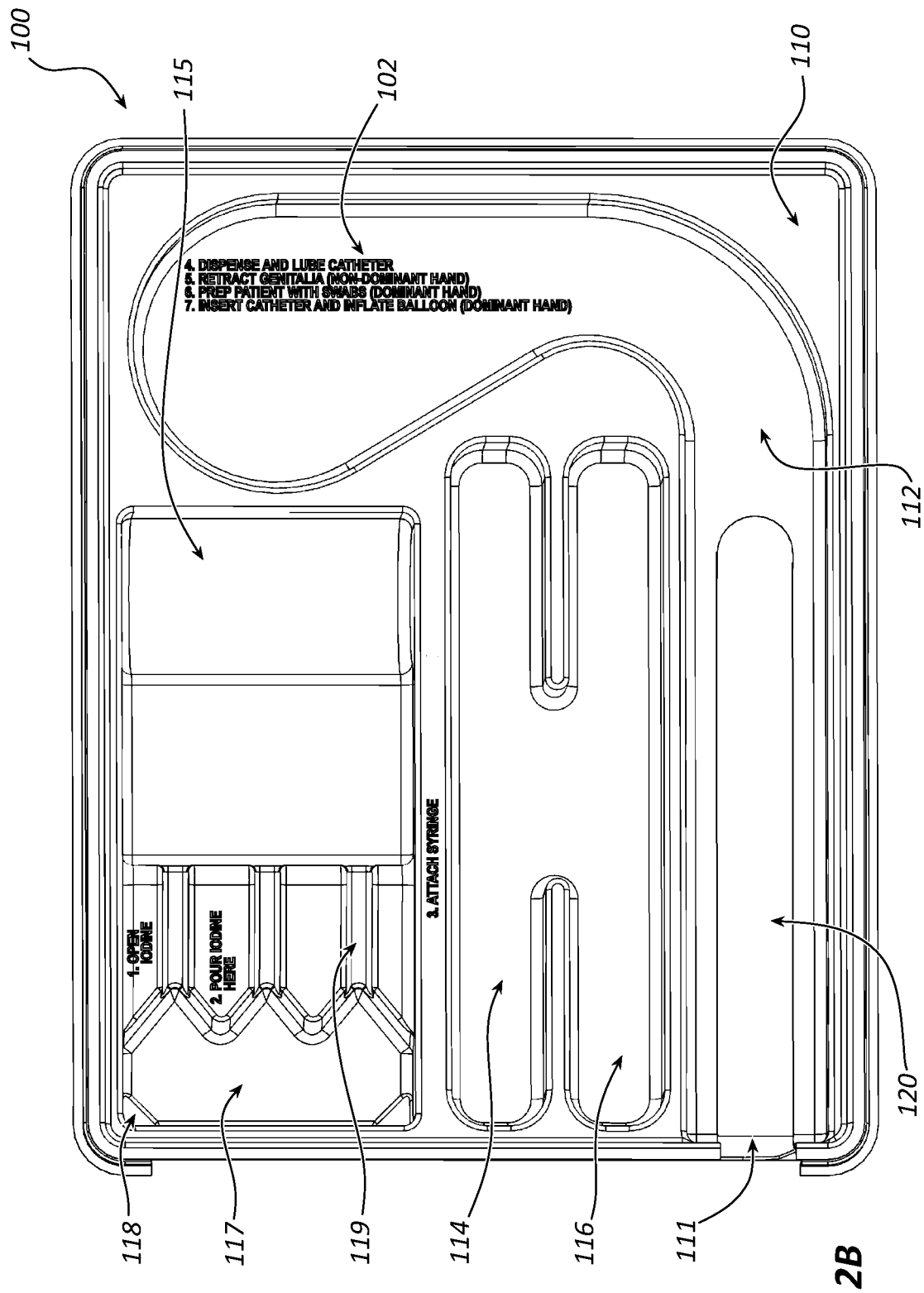
FIG. 2B provides a top view of the nested trays of FIG. 2A.
Figure 3A:
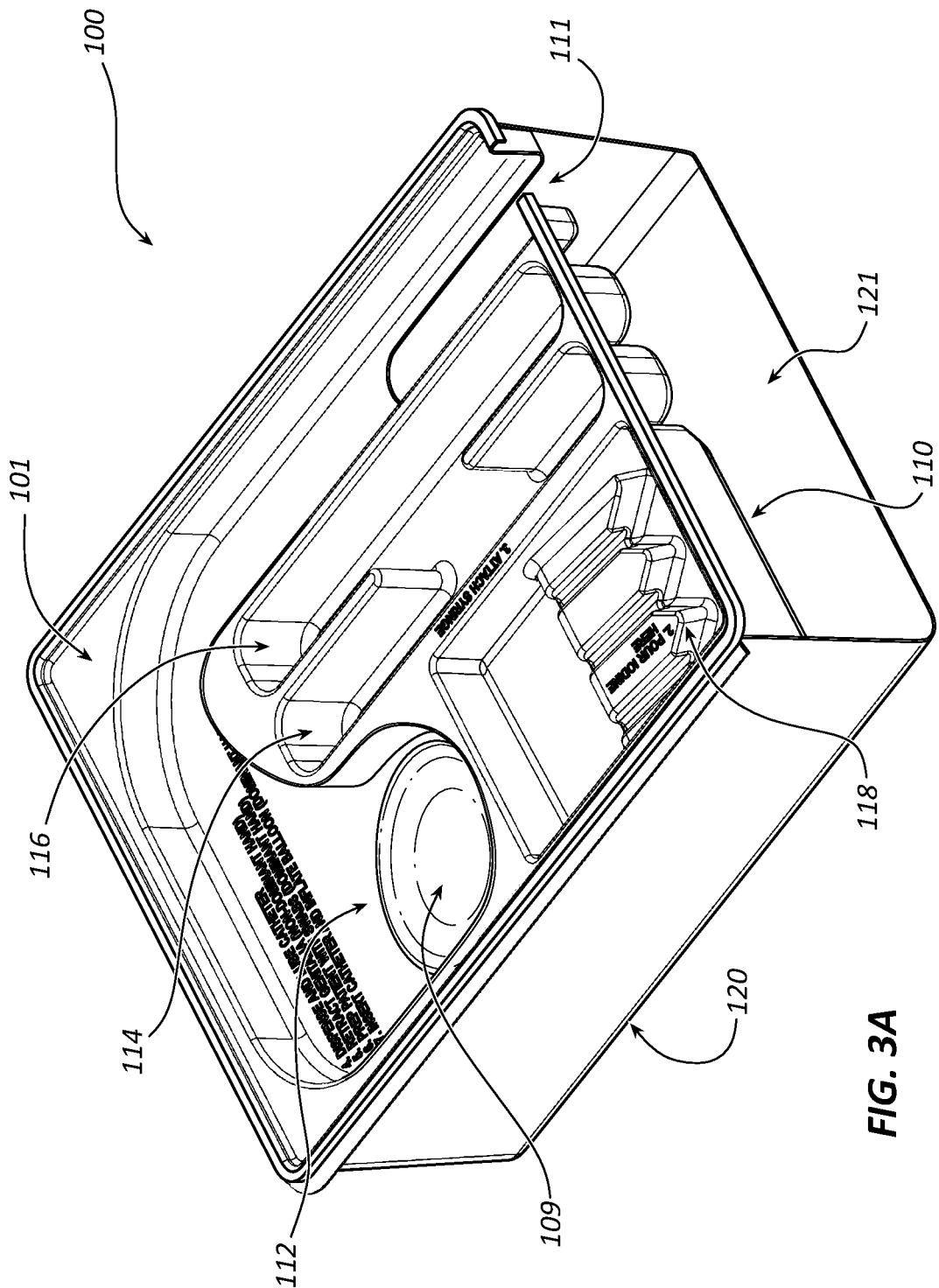
FIG. 3A provides a perspective view of alternative nested trays of a urinary catheter-insertion kit in accordance with some embodiments.
Figure 3B:
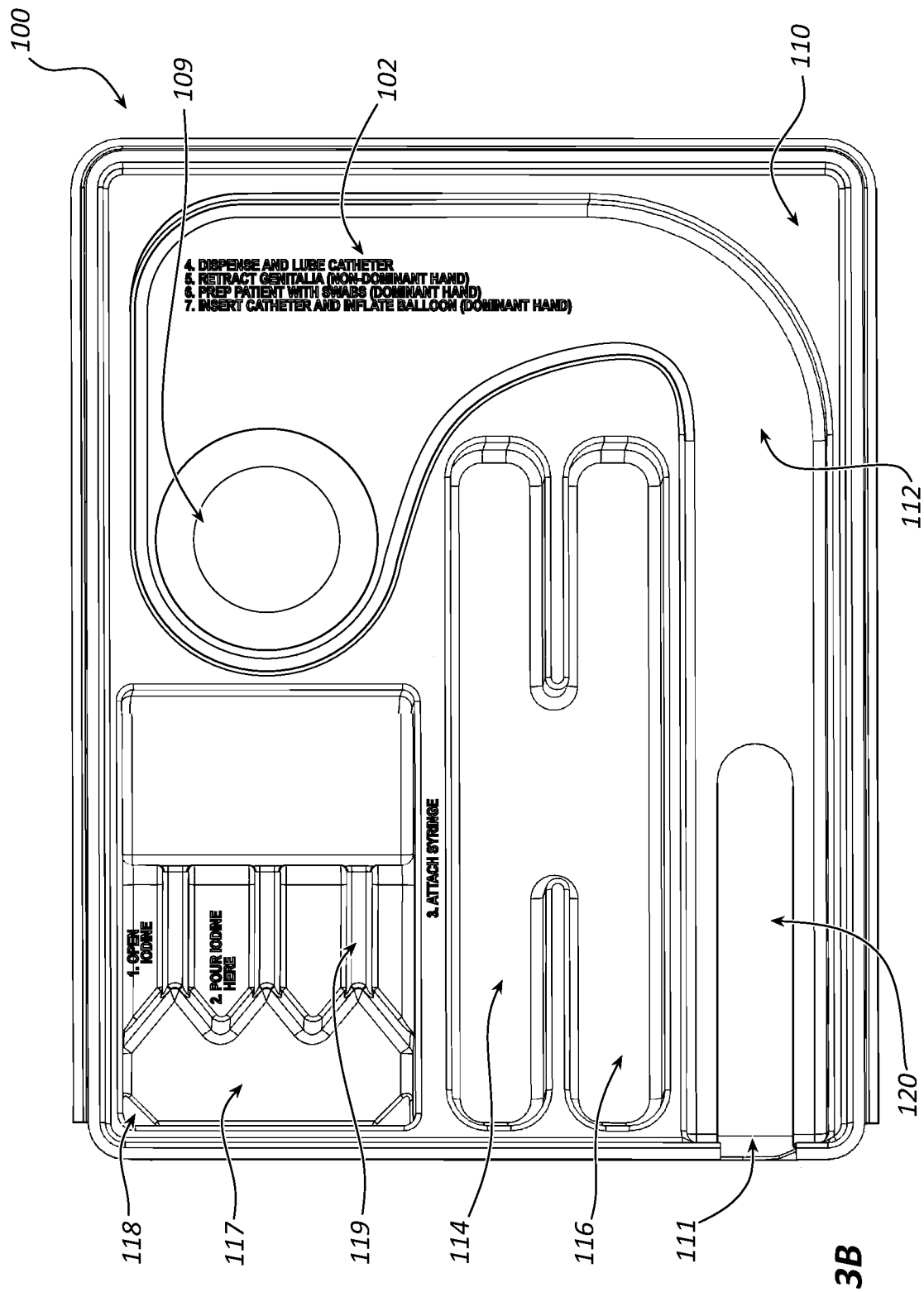
FIG. 3B provides a top view of the nested trays of FIG. 3A.
Figure 6A:
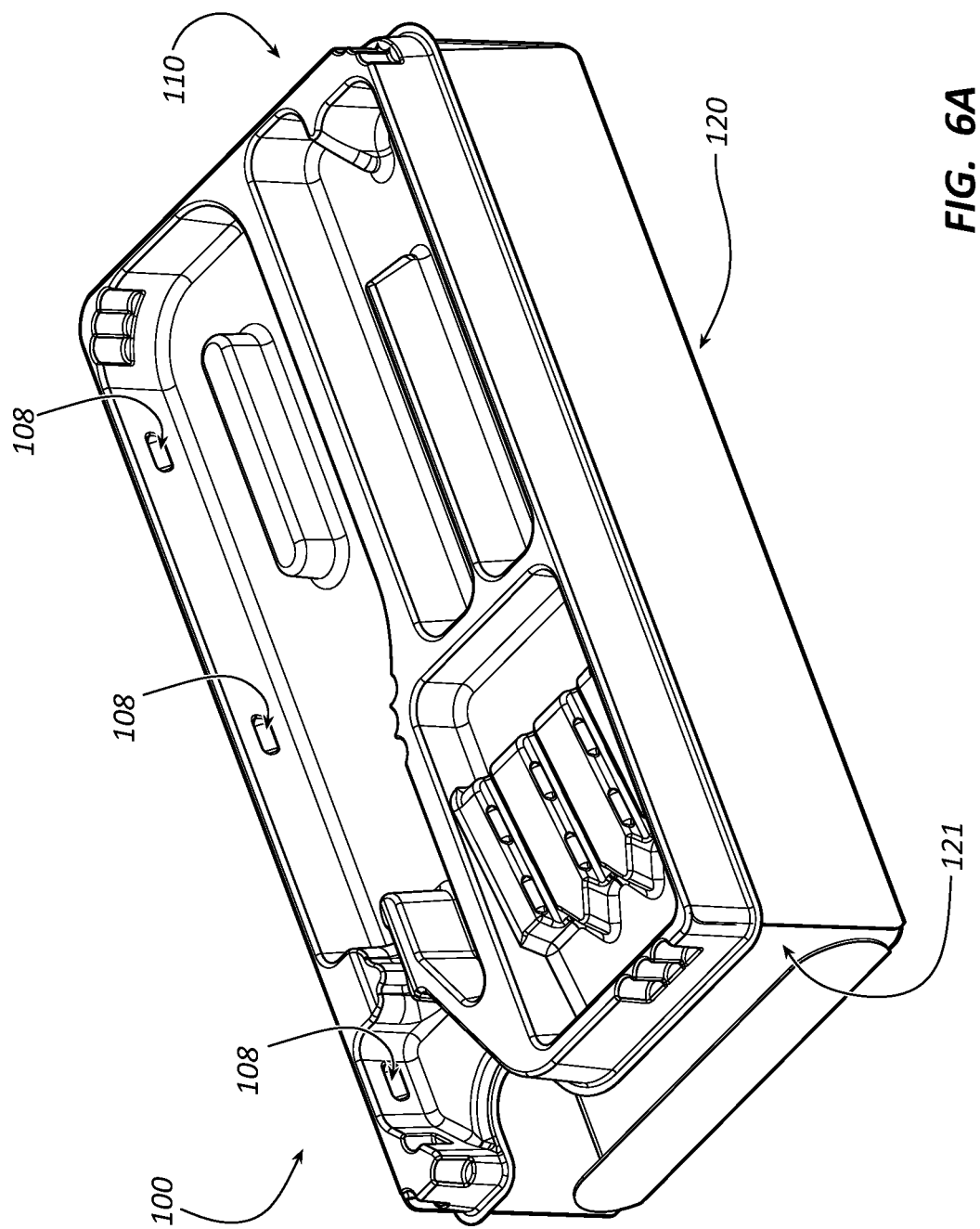
FIG. 6A provides a perspective view of alternative nested trays of a urinary catheter-insertion kit in accordance with some embodiments.

FIG. 1A provides a perspective view of a urinary catheter-insertion kit 100 including at least some components in a working tray 110 of the urinary catheter-insertion kit 100 in accordance with some embodiments. FIGS. 1B-1D provide different views of the urinary catheter-insertion kit 100 of FIG. 1A. Additional components not shown in FIGS. 1A-1D that are useful in the urinary catheter-insertion kit 100 can be found in U.S. Pat. Nos. 10,758,705 and 10,905,848, each of which is incorporated by reference in its entirety into this application. Such components can include, but are not limited to, any one or more components selected from a stabilization device (e.g., C. R. Bard, Inc.'s StatLock® Foley stabilization device), prepping balls (e.g., absorbent cotton balls), forceps, a label that can be filled out with catheterization or urine-sampling details, a fenestrated drape to place over a patient, an underpad to place under the patient, gloves (e.g., a package of latex or latex-free gloves), a sterile wrap (e.g., Central Supply Room ["CSR"] wrap) to wrap around the working and storage trays, a belly band (e.g., to hold the sterile wrap in place around the working and storage trays), hand sanitizer, moist towelettes (e.g., a package of castile-soap towelettes), additional instructions to those imprinted on at least the working tray (e.g., an instruction sheet for a clinician, an instruction pamphlet for the patient, etc.), a checklist of safety considerations, a patient information chart, an insert sheet, and a packaging label. FIGS. 2A and 2B provide different views of alternative nested trays of the urinary catheter-insertion kit 100 in accordance with some embodiments. FIGS. 3A and 3B provide different views of further alternative nested trays of the urinary catheter-insertion kit 100 in accordance with some embodiments. FIG. 6A provides a perspective view of yet further alternative trays of the urinary catheter-insertion kit 100 in accordance with some embodiments.

The urinary catheter-insertion kit 100 can include a working tray 110, a storage tray 120, a urinary catheter 132 (e.g., a Foley catheter), and a drainage system (not shown) including drainage tubing and a drainage receptacle (e.g., drainage bag, optionally including a urine meter). (See U.S. Pat. Nos. 10,758,705 and 10,905,848 for description of the drainage system, which can include a urine meter in addition to the drainage tubing and the drainage receptacle.)

The working tray 110 can be configured to nest with the storage tray 120 by suspending the working tray 110 from the storage tray 120. At least the working tray 110 can include a number of preformed sections configured to respectively hold a number of components of the urinary catheter-insertion kit 100. For example, at least one section of the preformed sections of the working tray 110 can include a catheter section 112 configured to hold the catheter 132.

The storage tray 120 can include an opening such as a cutout 121 in an end of the storage tray 120. The opening such as the cutout 121 in the end of the storage tray 120 can be configured to facilitate access to any of the components of the urinary catheter-insertion kit 100 stored in the storage tray 120 while working from the working tray 110. For example, until needed, the drainage system can be stored in the storage tray 120 while working from the working tray 110. The opening or the cutout 121 also allows access to a bottom of the working tray 110, if needed, to lift the working tray 110 out of the storage tray 120 while supporting the bottom of the working tray 110. That said, the working tray 110 can be fixed (e.g., fastened, bonded, etc.) to the storage tray 120 in some embodiments. In such embodiments, the urinary catheter-insertion kit 100 is designed such that the working tray 110 remains fixed to the storage tray 120 throughout a catheterization procedure. Indeed, as shown in FIG. 6B, an instruction can be included along with step-by-step catheterization instructions imprinted directly on at least the working tray 110 to not separate the working tray 110 from the storage tray 120.

Figure 6C:
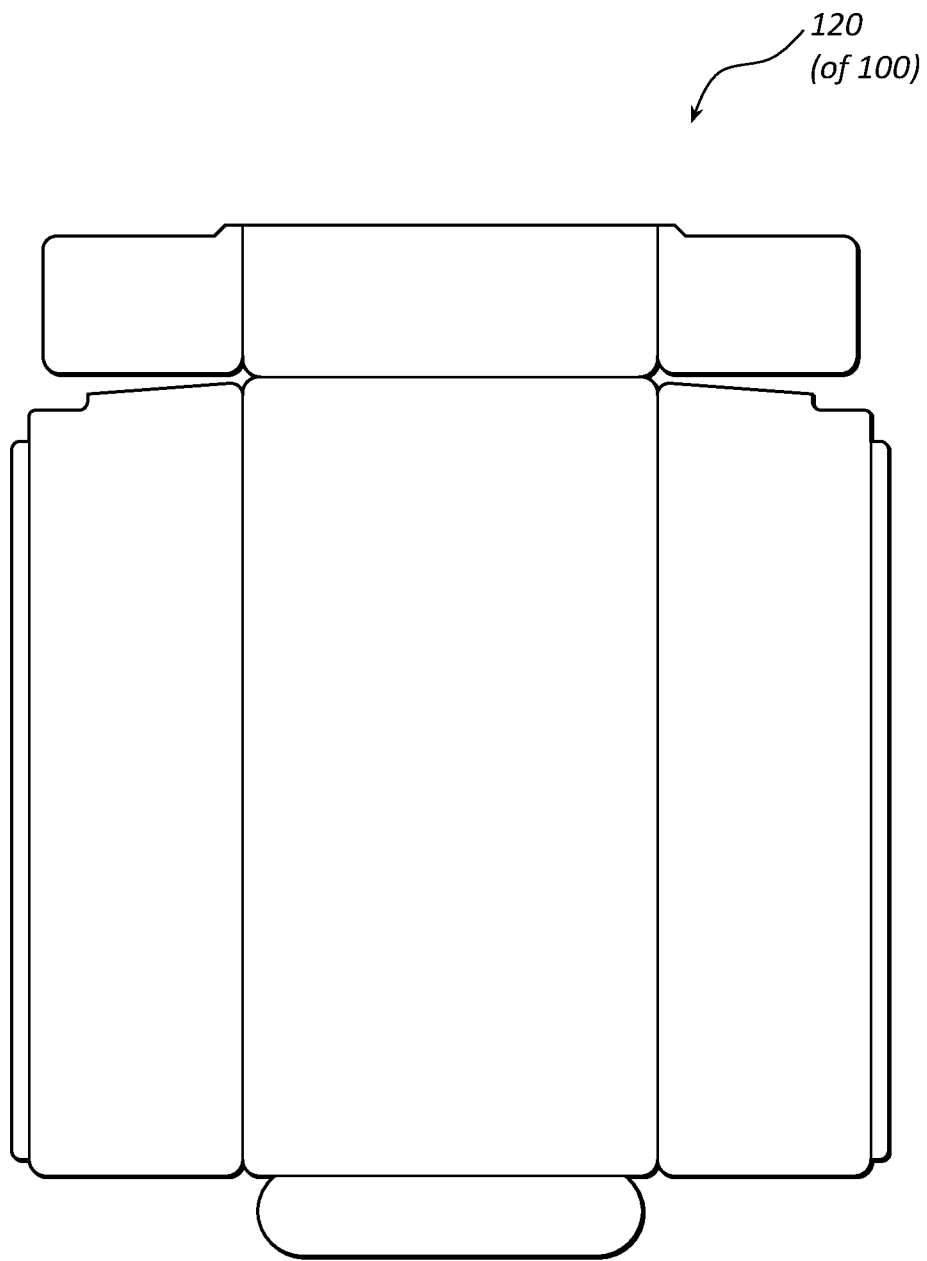
FIG. 6C provides a top view of an unfolded paperboard precursor of an alternative storage tray of a urinary catheter-insertion kit in accordance with some embodiments.
Figure 7:
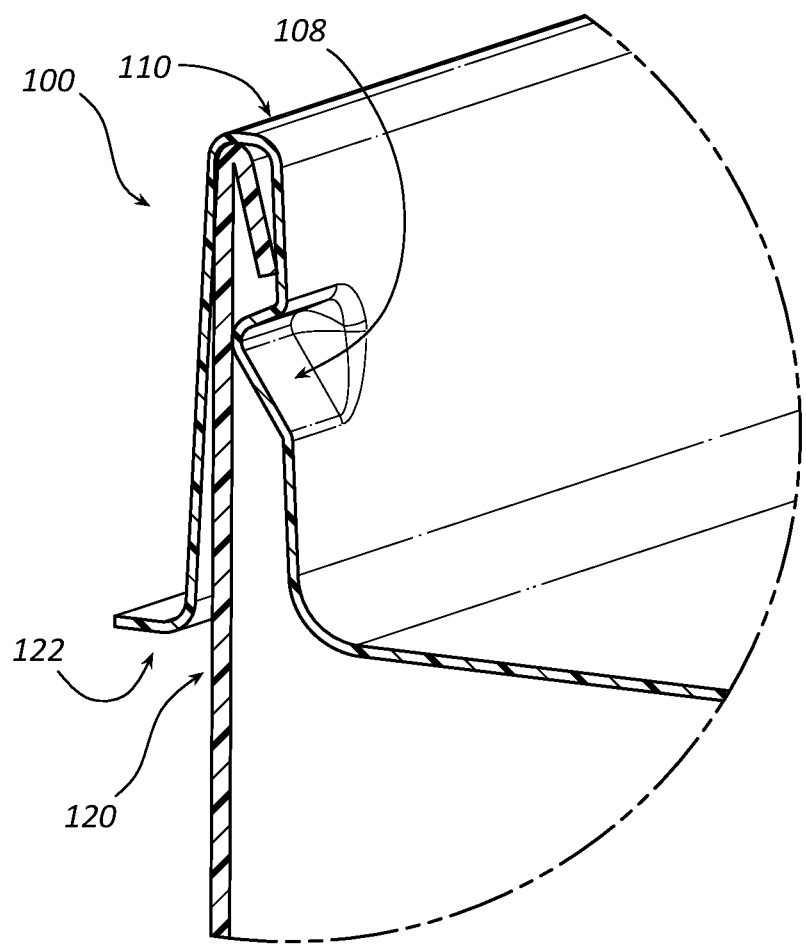
FIG. 7 provides a cross section of a tray fastening mechanism for fastening together the alternative nested trays of FIG. 6A in accordance with some embodiments.

The storage tray 120 of FIG. 6A is a folded paperboard storage tray of the urinary catheter-insertion kit 100. FIG. 6C provides an unfolded paperboard precursor to the foregoing folded paperboard storage tray. Once the paperboard precursor is folded along the fold lines shown, the resulting storage tray 120 includes folded-over longitudinal edges configured to engage a number of protrusions (see FIG. 6A) molded into the working tray 110, thereby forming a portion of a fastening mechanism (see FIG. 7) for fastening together the working tray 110 and the storage tray 120. As an alternative to the folded-over longitudinal edges, the paperboard precursor of FIG. 6C can include a number of tabs along the longitudinal edges thereof configured to form upon folding the paperboard precursor a number of folded-over tabs configured to engage the number of protrusion molded into the working tray 110.

The working tray 110 can include a cutout 111 in a corner area of the catheter section 112 formed between a bottom portion and an end portion of the catheter section 112. The cutout 111 in the corner area of the catheter section 112 can be configured to allow, for example, the drainage tubing of the drainage system to pass from the storage tray 120 to the working tray 110 by way of a bottom of the cutout 111 when the drainage tubing is stored in the storage tray 120. A side of the cutout 111 in the corner area of the catheter section 112 can be configured to allow the drainage tubing to be removed from the storage tray 120 without disconnecting the drainage tubing from the catheter 132 when the drainage system and the catheter 132 are pre-connected in the urinary catheter-insertion kit 100 as set forth below. In contrast, if the end portion of the catheter section 112 is intact and the cutout 111 consists of only the bottom portion of the catheter section 112 (i.e., the cutout 111 is a hole in the bottom portion of the catheter section 112), the drainage tubing and, subsequently, the catheter 132 would have to be pulled through the cutout 111 when the drainage system and the catheter 132 are pre-connected, which risks contamination of the catheter 132. Alternatively, the drainage tubing would have to be disconnected from the catheter 132 when the drainage system and the catheter 132 are pre-connected, which also risks contamination of the catheter 132 by way of either disconnecting the drainage tubing from the catheter 132 or reconnecting the drainage tubing to the catheter 132.

Figure 6B:
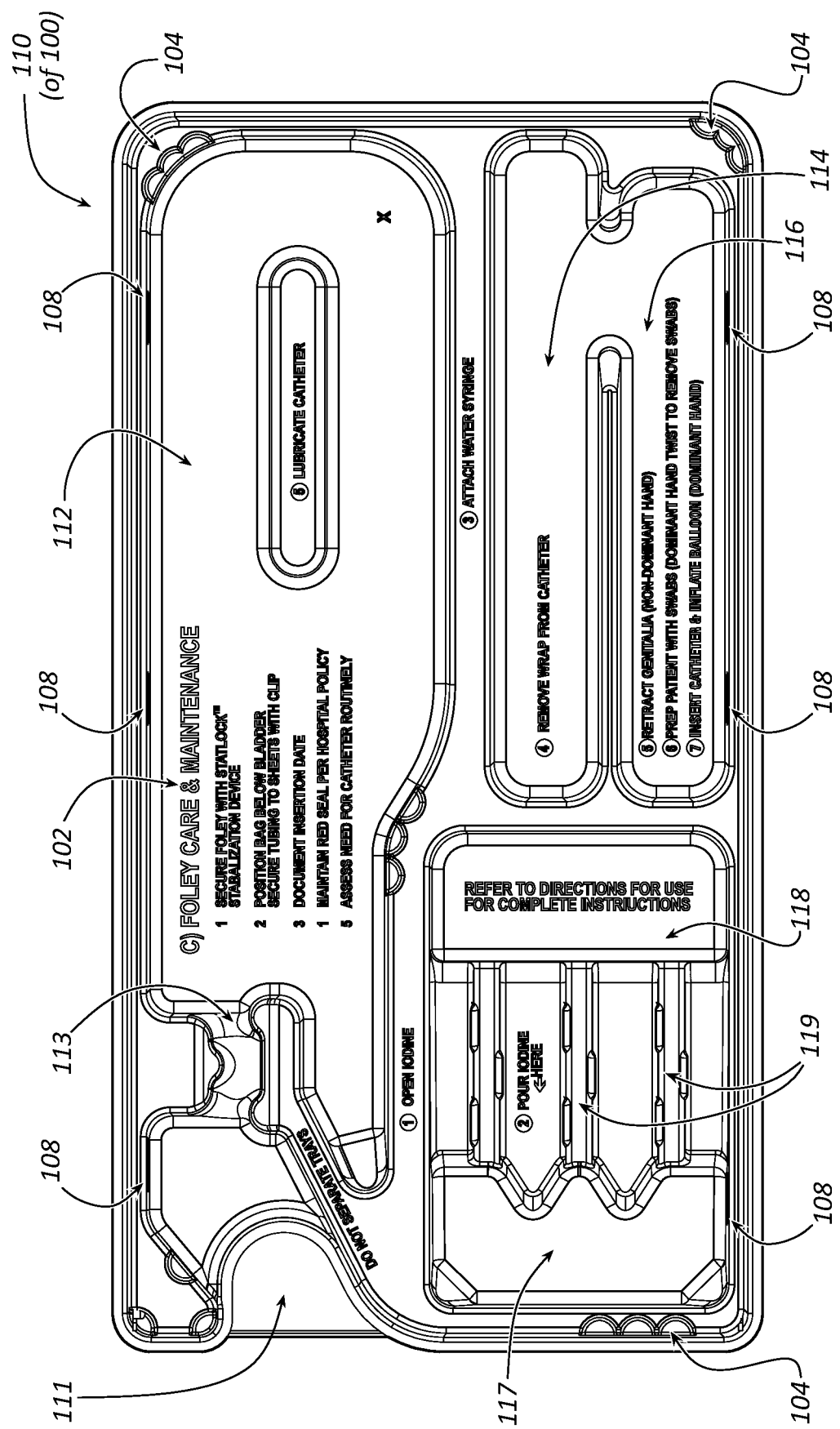
FIG. 6B provides a top view of an alternative working tray of a urinary catheter-insertion kit in accordance with some embodiments.

The working tray 110 can include a drainage-tubing constriction 113 between the cutout 111 in the corner area of the catheter section 112 and a remainder of the catheter section 112 as shown in FIG. 6B. The drainage-tubing constriction 113 can be configured to hold a portion of the drainage tubing when the drainage system and the catheter 132 are pre-connected. By holding the drainage tubing in the drainage-tubing constriction 113, an initial or as-manufactured placement of the foregoing pre-connected urinary catheter 132 in the working tray 110 can be maintained until the urinary catheter 120 is used for urinary catheterization. As shown, the drainage-tubing constriction 113 can include snap-in tabs configured to hold the drainage tubing in the drainage-tubing constriction 113.

The working tray 110 can include a number of lugs 104 projecting from a bottom side of the working tray 110. Each lug of the number of lugs 104 also forms a well in a top side of the working tray 110 as shown in FIG. 6A. Notably, while the number of lugs 104 are shown in sets of three about the working tray 110 such as the four sets of three lugs 104 respectively at or near the four corners of the working tray 110, only one lug of each set of lugs 104 is present in any particular working tray 110. For example, a first lug of each set of lugs 104 can be present in a first working tray 110, a second lug of each set of lugs 104 can be present in a second working tray 110, and a third lug of each set of lugs 104 can be present in a third working tray 110, not one of which working trays matches another on account of the number of lugs 104. Indeed, the number of lugs 104 are configured to prevent two or more working trays including the number of lugs 104 to nest too tightly together such as after molding (e.g., thermoforming) two or more of the foregoing working trays and nesting them together.

The working tray 110 can include a number of indentations 108 in at least longitudinal sides of the working tray 110, as viewed from within a working area of the working tray 110. (See, for example, FIGS. 6A and 7.) The number of indentations 108 correspondingly provide a number of projections between at least the longitudinal sides of the working tray 110 and an overhang 122 (see FIG. 7) of the working tray 120, thereby forming another portion of the fastening mechanism for fastening together the working tray 110 and the storage tray 120. With the overhang 122, the working tray 110 is configured for insertion of the folded-over longitudinal edges or tabs of the storage tray 120 of FIG. 6A in a gap between the longitudinal sides of the working tray 110 and the overhang 122. As shown, the number of projections provided by way of the number of indentations 108 are configured to engage the folded-over longitudinal edges or tabs of the storage tray 120, thereby fastening together the working tray 110 and the storage tray 120 and preventing separation thereof. Notably, the gap between the longitudinal sides and the overhang 122 of the working tray 110 are dimensioned to provide the folded-over longitudinal edges or tabs of the storage tray 120 room to expand under a spring force within folds of the folded-over longitudinal edges or tabs created by forcing the longitudinal edges or tabs into longitudinal sides of the paperboard of the storage tray 120. In addition, the number of protrusions protrude as sharply as molding (e.g., thermoforming) allows making engaging surfaces of the number of protrusions as flat as possible for engaging the folded-over longitudinal edges or tabs of the storage tray 120. The foregoing fastening mechanism shown in FIG. 7 obviates a need for a secondary mechanism (e.g., bonding) for fastening the working tray 110 and the storage tray 120 together.

The catheter 132 can be pre-connected to the drainage system to minimize any potential failures in connecting the catheter 132 to the drainage system, which, in turn, can minimize any potential contamination. Between the catheter 132 and the drainage tubing, a connector 134 can be used to connect the catheter 132 and the drainage tubing. The connector 134 can include a urine-sampling port configured to facilitate urine sampling.

At least one section of the preformed sections of the working tray 110 can include a lubricant well 109 configured to hold lubricant dispensed into the lubricant well 109 for lubricating the catheter 132. For example, the embodiments of FIGS. 1A-1D, 3A, and 3B include the lubricant well 109 as part of the catheter section 112. Alternatively, the working tray 110 does not include the lubricant well 109 but includes another section additionally configured for lubricating the catheter 132. For example, the embodiment of FIGS. 2A and 2B do not include the lubricant well 109 as part of the catheter section 112 but include additional space in place of the lubricant well 109 to hold dispensed lubricant for lubricating the catheter 132.

The urinary catheter-insertion kit 100 can further include a lubricant container 136 (e.g., syringe, packet, pod, vial, etc.) including, containing, or filled with lubricant for the catheter 132. At least one section of the preformed sections of the working tray 110 can include a lubricant-container section 114 (e.g., lubricant-syringe section, lubricant-packet section, lubricant-pod section, lubricant-vial section, etc.) configured to hold the lubricant container 136. The lubricant-container section 114 can be preformed to accommodate the lubricant container 136; however, the lubricant-container section 114 need not conform to every feature of the lubricant container 136. For example, if the lubricant container 136 is a syringe, the lubricant-container section 114 (e.g., lubricant-syringe section) need not include a recess for a flange of the syringe. That is, the lubricant-container section 114 can have a constant width or depth commensurate with at least the flange of the syringe to accommodate the syringe. Indeed, the lubricant-container section 114 can have a constant width or depth commensurate with the greatest width or diameter of any type lubricant container 136 set forth herein.

The urinary catheter-insertion kit 100 can further include an inflatant container 138 (e.g., syringe) including, containing, or filled with an inflatant (e.g., saline) for inflating a balloon of the catheter 132. At least one section of the preformed sections of the working tray 110 can include an inflatant-container section 116 (saline-syringe section) configured to hold the inflatant container 138. The inflatant-container section 116 can be preformed to accommodate the inflatant container 138; however, the inflatant-container section 116 need not conform to every feature of the inflatant container 138. For example, if the inflatant container 138 is a syringe, the inflatant-container section 116 (e.g., saline-syringe section) need not include a recess for a flange of the syringe. That is, the inflatant-container section 116 can have a constant width or depth commensurate with at least the flange of the syringe to accommodate the syringe. Indeed, the inflatant-container section 116 can have a constant width or depth commensurate with the greatest width or diameter of any type inflatant container 138 set forth herein.

As shown, the lubricant-container section 114 and the inflatant-container section 116 can be commensurate in shape and size. For example, the lubricant-container section 114 and the inflatant-container section 116 can have a same length, width, depth from common top surface of the working tray 110, or a combination thereof. Alternatively, each of the lubricant-container section 114 and the inflatant-container section 116 can have a different shape or size as shown in FIG. 6B. An opening between the lubricant-container section 114 and the inflatant-container section 116 as shown in each figure of FIGS. 1B, 2B, 3B, 4B, and 6B provides an access space configured for a lateral approach to scooping up the lubricant container 136 or the inflatant container 138 with one or more fingers and removing it from the working tray 110. If either container of the lubricant container 136 or the inflatant container 138 is a syringe, the lateral approach obviates handling the syringe by way of a longitudinal approach, which prevents accidental dispensation of the lubricant or the inflatant by pushing a plunger of the syringe into a barrel thereof. Since each section of the lubricant-container section 114 and the inflatant-container section 116 is commensurate with the greatest width or diameter of the lubricant container 136 or the inflatant container 138, the opening can be anywhere along a length of the foregoing sections. That is, the opening is not needed to accommodate any portion of either one of the lubricant container 136 or the inflatant container 138. However, to further prevent accidental dispensation of the lubricant or the inflatant when either the lubricant container 136 or the inflatant container 138 is a syringe, it is beneficial to have the opening around the barrel of the syringe to promote handling the syringe by the barrel.

The urinary catheter-insertion kit 100 can further include a genital-preparation kit including a package of an antiseptic (not shown) and one or more swab sticks 144. (See U.S. Pat. Nos. 10,758,705 and 10,905,848 for description of the genital-preparation kit.) At least one section of the preformed sections of the working tray 110 can include a genital-preparation section 118 configured with a well 117 to hold the antiseptic (e.g., povidone-iodine solution) from the package. The genital-preparation section 118 can also include one or more angled channels 119 to respectively hold the one or more swab sticks 144 with their corresponding one or more absorbent heads in the well 117. The well 117 is dimensioned to have a volume commensurate with an entire volume of the antiseptic from the package plus a volume of the one or more absorbent heads such that the one or more absorbent heads become saturated with the antiseptic when the antiseptic from the package is dispensed in the well 117. As shown, the one or more angled channels 119 can include snap-in tabs 121 configured to hold the one or more swab sticks respectively in the one or more angled channels 119.

The urinary catheter-insertion kit 100 can further include a urine-sampling container 152. At least one section of the preformed sections of the working tray 110 can include a urine sampling-container section 115 configured to hold the urine-sampling container 152. (See the embodiments of FIGS. 1A-1D, 2A, and 2B.) Alternatively, the storage tray 120 can be configured to hold the urine-sampling container 152 instead of the working tray 110. (See, for example, the embodiment of FIGS. 3A and 3B, which does not include the urine sampling-container section 115 in the working tray 110.) Configuring the storage tray 120 to hold the urine-sampling container 152 instead of the working tray 110 minimizes a height of the working tray 110.

The urinary catheter-insertion kit 100 can further include step-by-step catheterization instructions 102 imprinted directly on at least the working tray 110. At least some of the instructions 102 can be placed in a location that expressly or implicitly suggests by way of the location how to perform a step of the catheterization. For example, the genital-preparation section 118 can include an express instruction in the genital-preparation section 118 such as in the well 117 for dispensing the antiseptic from the package thereof into the well 117. (See, for example, FIG. 2B.) For example, the catheter section 112 can include an implicit instruction in the catheter section 112 for dispensing the lubricant into the catheter section 112 for lubricating the catheter 132. (See, for example, the instruction on the support in the middle of the catheter section 112 of the working tray 110 of FIG. 6B.) At least some of the instructions 102 can be revealed in step with steps of the catheterization. For example, removing the package of antiseptic from the genital-preparation section 118 can reveal the instruction to dispense the antiseptic from the package into the well 117 of the genital-preparation section 118 for saturating the one or more absorbent heads of the corresponding one or more swab sticks with the antiseptic. Revealing steps of the catheterization instructions 102 in this way does not overwhelm the clinician preforming the catheterization with too many steps at once.

The urinary catheter-insertion kit 100 can further include protective paperboard (not shown) configured to protect at least the components of the working tray 110. The working tray 110 can include a lip 101 around a perimeter of the working tray 110 configured to hold the paperboard.

The urinary catheter-insertion kit 100 can further include a peri-care kit (not shown). (See U.S. Pat. Nos. 10,758,705 and 10,905,848, each of which is incorporated by reference in its entirety herein, for description of the peri-care kit.) The urinary catheter-insertion kit 100 can be configured to include the peri-care kit between the paperboard and an outer packaging (e.g., Tyvek®) of the urinary catheter-insertion kit 100.

As such the urinary catheter-insertion kit 100 includes, in some embodiments, the working tray 110 including the urinary catheter 132, the lubricant container 136 including a lubricant for lubricating the catheter 132, the inflatant container 138 including an inflatant for inflating a balloon of the catheter 132, and a genital-preparation kit including a package of an antiseptic and the one or more swab sticks 144; the storage tray 120 including a drainage system including drainage tubing and a drainage receptacle; the step-by-step catheterization instructions 102 imprinted directly on at least the working tray 110; and an outer packaging of Tyvek® around the urinary catheter-insertion kit 100. At least the working tray 110 includes a number of preformed sections respectively holding a number of components of the urinary catheter-insertion kit 100. The preformed sections of the working tray 110 include at least the catheter section 112 including the catheter 132, the lubricant-container section 114 including the lubricant container 136, the inflatant-container section 116 including the inflatant container 138, and the genital-preparation section 118 including the package of the antiseptic and the one or more swab sticks 144. The preformed sections of the working tray 110 include the step-by-step catheterization instructions 102 imprinted directly on at least the working tray 110 without express identification on the working tray 110 of the number of components.

The catheter section 112 is configured to hold the lubricant dispensed from the lubricant container 136 when lubricating the catheter 132. The lubricant-container section 114 and the inflatant-container section 116 have the same constant depth from the common top surface of the working tray 110. The genital-preparation section 118 is configured with the well 117 to hold the antiseptic from the package. The genital-preparation section 118 also includes the one or more angled channels 119 holding the one or more swab sticks 144 with their absorbent heads in the well 118. The working tray 110 is fixed to the storage tray 120 in a nested configuration in which the working tray 110 is suspended from the storage tray 120. The working tray 110 includes the cutout 111 in the corner area of the catheter section 112 formed between a bottom portion and an end portion of the catheter section 112. The drainage system is pre-connected to the catheter 132 through the connector 134 having the urine-sampling port. The cutout 111 in the corner area of the catheter section 112 is configured to allow the drainage tubing to pass from the storage tray 120 where the drainage system is stored to the working tray 110 by way of a bottom of the cutout 111 in the corner area of the catheter section 112.

As such the urinary catheter-insertion kit 100 also includes, in some embodiments, the working tray 110 including a Foley catheter, a lubricant-filled syringe for lubricating the catheter 132, a saline-filled syringe for inflating a balloon of the catheter 132, a genital-preparation kit including a package of an antiseptic and the one or more swab sticks 144, and the urine-sampling container 152; the storage tray 120 including a drainage system including drainage tubing and a drainage receptacle; and the step-by-step catheterization instructions 102 imprinted directly on at least the working tray 110. At least the working tray 110 includes a number of preformed sections respectively holding a number of components of the urinary catheter-insertion kit 100. The preformed sections of the working tray 110 include at least the catheter section 112 including the catheter 132, a lubricant-syringe section including the lubricant-filled syringe, a saline-syringe section including the saline-filled syringe, and the genital-preparation section 118 including the package of the antiseptic and the one or more swab sticks 144. At least one section of the preformed sections of the working tray 110 includes the urine sampling-container section 115 including the urine-sampling container 152.

Alternatively, the storage tray 120 is configured to hold the urine-sampling container 152 instead of the working tray 110. The genital-preparation section 118 is configured with the well 117 to hold the antiseptic from the package. The genital-preparation section 118 also includes the one or more angled channels 119 holding the one or more swab sticks 144 with their absorbent heads in the well 118. The working tray 110 is configured to nest with the storage tray 120 by suspending the working tray 110 from the storage tray 120. The working tray 110 includes the cutout 111 in the corner area of the catheter section 112 formed between a bottom portion and an end portion of the catheter section 112. The drainage system is pre-connected to the catheter 132 through the connector 134 having the urine-sampling port. The cutout 111 in the corner area of the catheter section 112 is configured to allow the drainage tubing to pass from the storage tray 120 where the drainage system is stored to the working tray 110 by way of a bottom of the cutout 111 in the corner area of the catheter section 112.

Figure 4A:
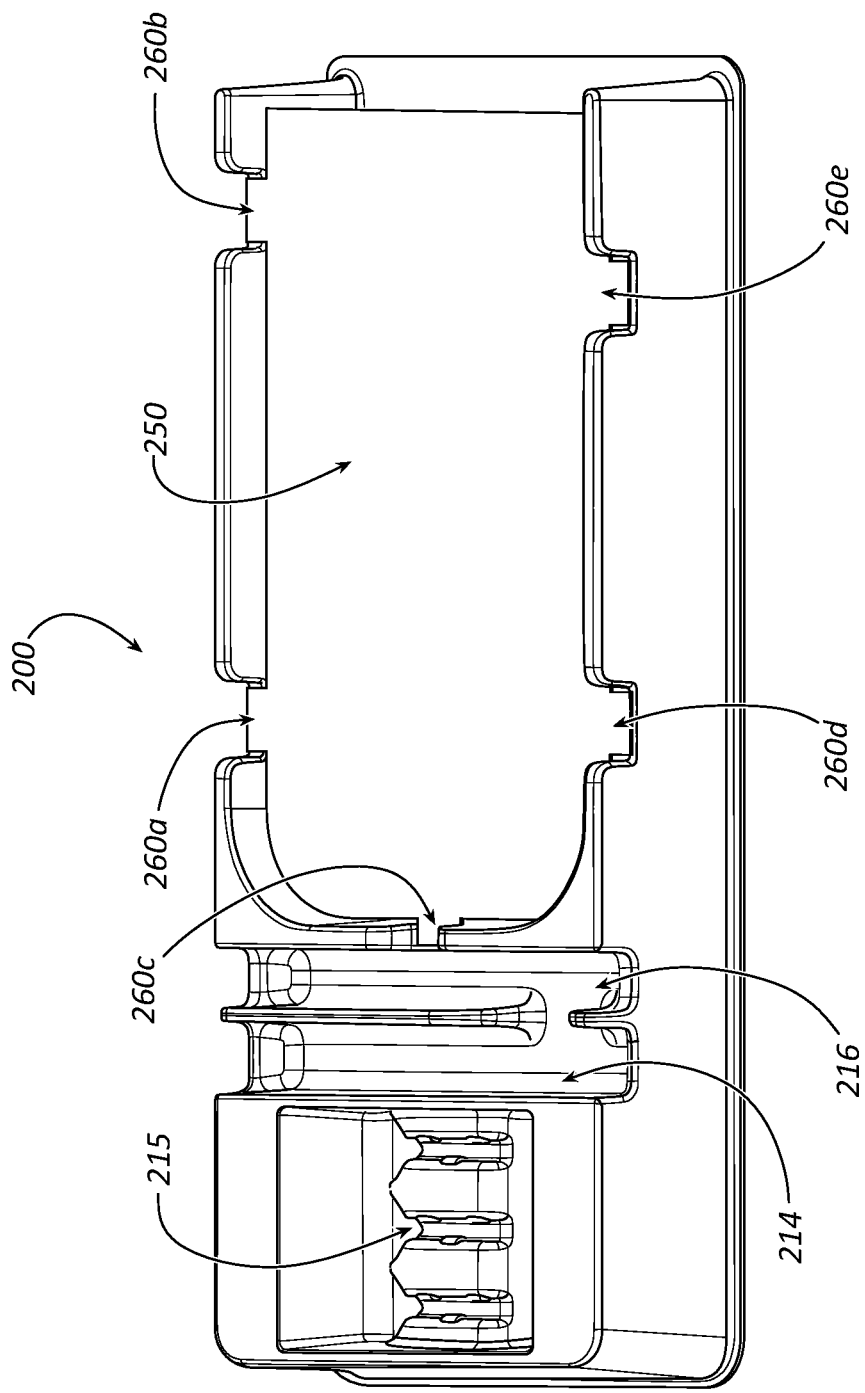
FIG. 4A illustrates a perspective view of a urinary catheter-insertion kit.

FIG. 4A illustrates another embodiment of the present invention. Urinary catheter-insertion kit 200 includes a urine sampling container section 215, syringe compartment 214, a second syringe compartment 216, and a base 250 that separates the working tray from the storage tray. According to certain embodiments, the base 250 is configured to be secured to the working tray, e.g., the base 250 is not configured to be removed. Features 260a-260e are configured to assist in securely fastening the base 250 between the working and storage trays.

Figure 4B:
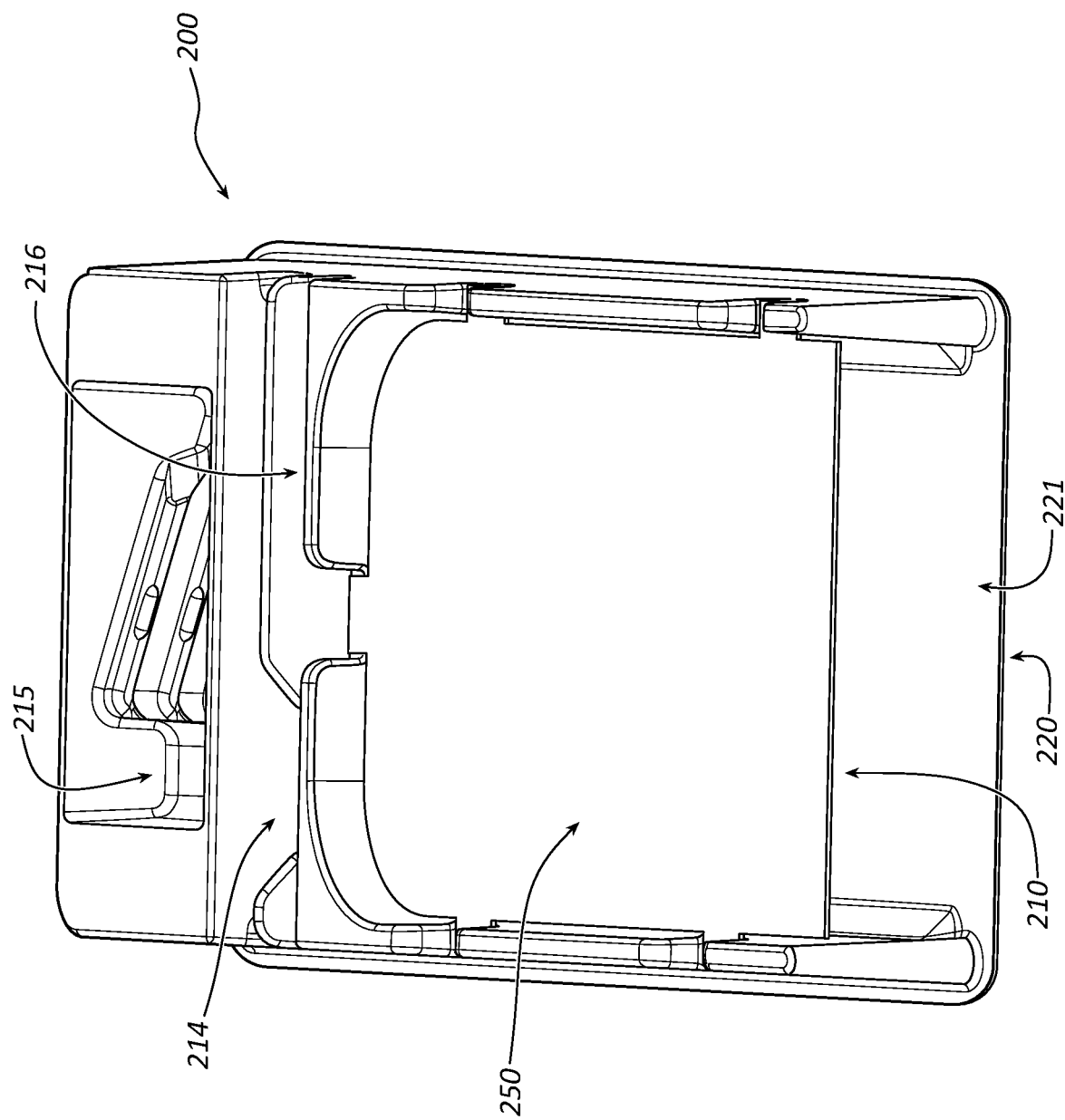
FIG. 4B illustrates another view of the urinary catheter-insertion kit.

FIG. 4B illustrates another embodiment of the tray of FIG. 4A, including working tray 210 and storage tray 220, which can include an opening 221 in an end of the storage tray 220.

Figure 5:
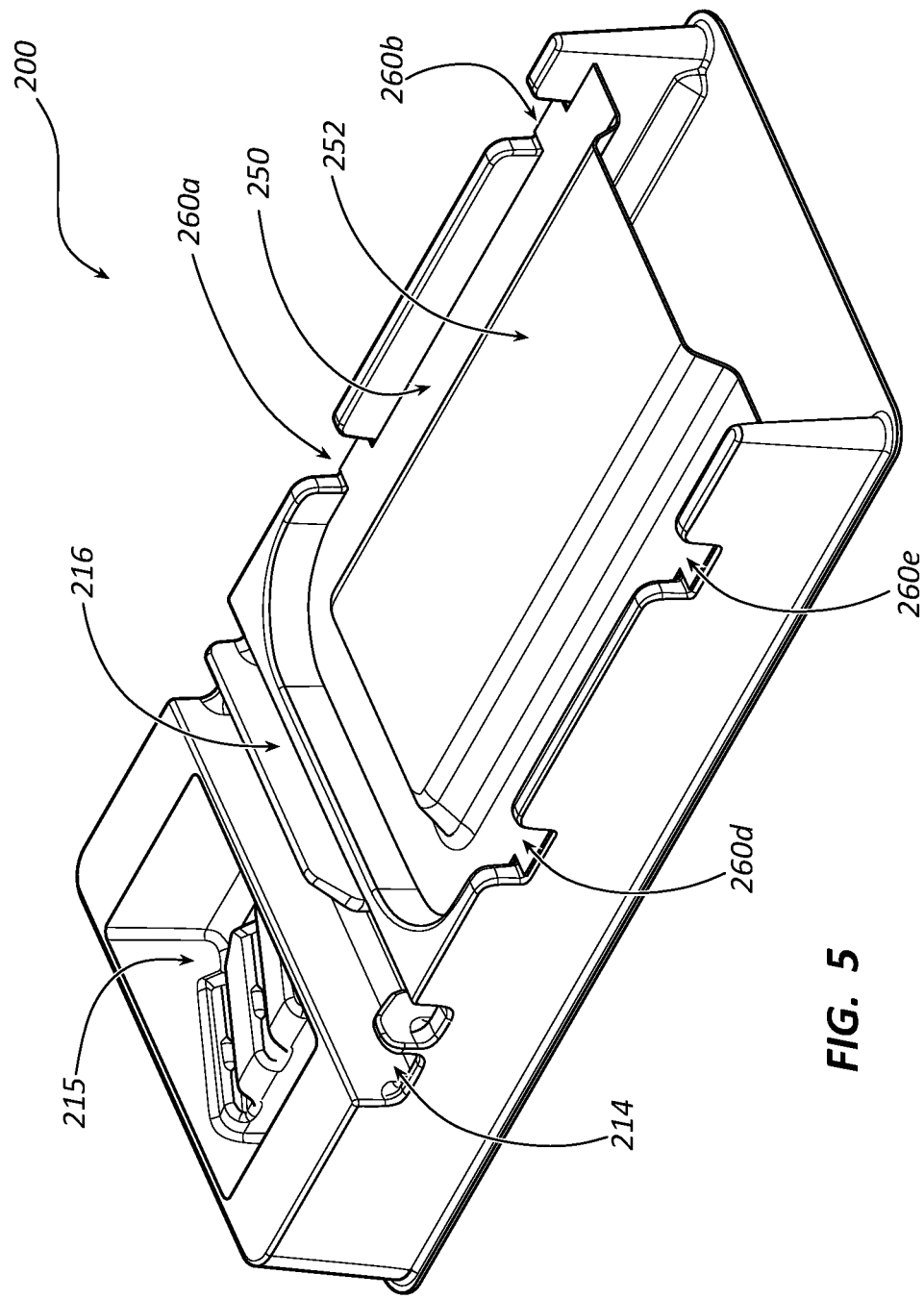
FIG. 5 illustrates a urinary catheter insertion kit in accordance with some embodiments.

FIG. 5 illustrates yet another embodiment of a catheter-insertion tray in accordance with the present disclosure. Base 250 has an elevated portion 252 allowing for more room in the storage tray. Moreover, feature 260c is absent according to this embodiment.

METHODS

Methods of urinary catheterization with a urinary catheter-insertion kit 100 can include, in some embodiments, removing an outer packaging from the urinary catheter-insertion kit 100, cleaning a patient's perianal area with a peri-care kit, preparing the patient's genital area using a genital-preparation kit, and catheterizing the patient with the catheter 132 (e.g., a Foley catheter). Removing the outer packaging from the urinary catheter-insertion kit 100 can bare the working tray 110 suspendedly nested with the storage tray 120 with the step-by-step catheterization instructions 102 imprinted directly on at least the working tray 110. The working tray 110 can include a number of preformed sections respectively holding a number of components for the method of urinary catheterization with the urinary catheter-insertion kit 100. Removing the outer packaging from the urinary catheter-insertion kit 100 can also bare a protective paperboard configured to protect the components of the urinary catheter-insertion kit 100 in the working tray 110 under the paperboard.

Cleaning the patient's perianal area with the peri-care kit can include removing the peri-care kit from between the outer packaging of the urinary catheter-insertion kit 100 and the paperboard over the working tray 110. Preparing the patient's genital area using the genital-preparation kit can include using a package of an antiseptic and the one or more swab sticks 144 of the genital-preparation kit. Preparing the patient's genital area can include removing the package of the antiseptic from the genital-preparation section 118 of the working tray 110, opening the package of the antiseptic, and dispensing the antiseptic into the well 117 of the genital-preparation section 118, thereby saturating one or more absorbent heads of the one or more corresponding swab sticks 144 respectively held in the one or more angled channels 119 of the genital-preparation section 118. Catheterizing the patient with the catheter 132 can include removing the catheter 132 from the catheter section 112 of the working tray 110 and a drainage system from the storage tray 120 without disconnecting the catheter 132 from either drainage tubing or a drainage receptacle of the drainage system.

The working tray 110 can include the cutout 111 in the corner area of the catheter section 112 formed between a bottom portion and an end portion of the catheter section 112. The cutout 111 can enable removing both the catheter 132 from the catheter section 112 of the working tray 110 and the drainage system from the storage tray 120 without disconnecting the catheter 132 from the drainage system. If the working tray 110 includes the drainage-tubing constriction 113, removing both the catheter 132 from the working tray 110 and the drainage system from the storage tray 120 includes removing the drainage tubing from the drainage-tubing constriction 113 in the working 110.

Opening the package of the antiseptic and dispensing the antiseptic into the well 117 of the genital-preparation section 118 of the working tray 110 can be in accordance with the step-by-step catheterization instructions 102 imprinted directly on the working tray 110. These catheterization instructions 102 are shown in FIGS. 2B and 3B as the first and second steps of the method imprinted directly on the working tray 110.

Preparing the patient's genital area can include retracting the patient's genitals using a non-dominant hand and swabbing the patient's genitals with the antiseptic using a dominant hand in accordance with the step-by-step catheterization instructions 102 imprinted directly on the working tray 110. These catheterization instructions 102 are shown in FIGS. 2B and 3B as the fifth and sixth steps of the method imprinted directly on the working tray 110.

The method can further include removing a lubricant-filled syringe from a lubricant-syringe section of the working tray 110, dispensing the lubricant from the lubricant-filled syringe into the lubricant-syringe section, the catheter section 112, or another preformed section of the working tray 110, and lubricating the catheter 132 with the lubricant dispensed in the working tray 110. At least dispensing the lubricant into a preformed section of the working tray 110 (e.g., the catheter section 112) and lubricating the catheter 132 with the lubricant dispensed in the working tray 110 can be in accordance with the step-by-step catheterization instructions 102 imprinted directly on the working tray 110. This catheterization instruction is shown in FIGS. 2B and 3B as the fourth step of the method imprinted directly on the working tray 110. Removing the lubricant-filled syringe from the lubricant-syringe section can reveal the catheterization instruction imprinted in a bottom of the lubricant-syringe section to dispense the lubricant from the lubricant-filled syringe into the catheter section 112 for lubricating the catheter 132. Revealing steps of the catheterization instructions 102 in this way keeps the clinician performing the catheterization from becoming overwhelmed by too many steps at once.

The method further can include removing a saline-filled syringe from a saline-syringe section of the working tray 110 and attaching the saline-filled syringe to the catheter 132 for inflating a balloon of the catheter 132. At least attaching the saline-filled syringe to the catheter 132 can be in accordance with the step-by-step catheterization instructions 102 imprinted directly on the working tray 110. This catheterization instruction is shown in FIGS. 2B and 3B as the third step of the method imprinted directly on the working tray 110.

Catheterizing the patient can include inserting the catheter 132 into the patient's urethra and inflating the balloon with saline from the saline-filled syringe. At least inflating the balloon with saline from the saline-filled syringe can be in accordance with the step-by-step catheterization instructions 102 imprinted directly on the working tray 110. This catheterization instruction is shown in FIGS. 2B and 3B as the seventh step of the method imprinted directly on the working tray 110.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A urinary catheter kit, comprising:
a urinary catheter assembly including a urinary catheter and a drainage system, the drainage system including drainage tubing and a drainage receptacle;
a plurality of urinary catheter components;
a storage tray configured to accommodate the drainage system; and
a working tray nested on the storage tray, the working tray including a plurality of preformed sections configured to accommodate the urinary catheter and the plurality of urinary catheter components, the plurality of preformed sections including a catheter section with an opening into the storage tray, wherein the drainage tubing is connected to the urinary catheter through the opening.

2. The urinary catheter kit according to claim 1, further comprising a protective paperboard configured to protect components of the urinary catheter kit.

3. The urinary catheter kit according to claim 2, wherein the working tray includes a lip around a perimeter configured to secure the protective paperboard.

4. The urinary catheter kit according to claim 1, wherein the storage tray includes an open end designed to facilitate access to the drainage system in the storage tray while working from the working tray.

5. The urinary catheter kit according to claim 4, wherein the opening of the catheter section extends through an end of the working tray to enable the drainage tubing to be removed from the storage tray from the open end of the storage tray without disconnecting the drainage tubing from the urinary catheter.

6. The urinary catheter kit according to claim 1, wherein the working tray includes a drainage-tubing constriction configured to hold a portion of the drainage tubing and maintain an initial placement of the urinary catheter in the working tray until the urinary catheter is ready for use.

7. The urinary catheter kit according to claim 1, wherein the plurality of unrinary catheter components comprise a connector including a urine-sampling port configured to connect the urinary catheter to the drainage tubing, wherein the connector is pre-connected to the urinary catheter in the urinary catheter kit.

8. The urinary catheter kit according to claim 1, wherein the plurality of urinary catheter components comprise a lubricant container including lubricant for the urinary catheter, wherein the plurality of preformed sections of the working tray include a lubricant-container section configured to hold the lubricant container.

9. The urinary catheter kit according to claim 1, wherein the plurality of urinary catheter components comprise an inflatant container including an inflatant for inflating a balloon of the urinary catheter, wherein the plurality of preformed sections of the working tray include an inflatant-container section configured to hold the inflatant container.

10. The urinary catheter kit according to claim 1, wherein the plurality of urinary catheter components comprise a genital-preparation kit including a package of an antiseptic and one or more swab sticks, wherein the plurality of preformed sections of the working tray include a genital-preparation section configured with a well to hold the antiseptic from the package and one or more angled channels to respectively hold the one or more swab sticks with their corresponding one or more absorbent heads in the well.

11. The urinary catheter kit according to claim 10, wherein the well is dimensioned to have a volume commensurate with an entire volume of the antiseptic from the package plus a volume of the corresponding one or more absorbent heads such that the one or more absorbent heads become saturated with the antiseptic when the antiseptic from the package is dispensed in the well.

12. The urinary catheter kit according to claim 1, wherein the plurality of urinary catheter components comprise a urine-sampling container, wherein the preformed sections of the working tray include a urine sampling-container section configured to hold the urine-sampling container.

13. The urinary catheter kit according to claim 1, wherein the plurality of urinary catheter components comprise a urine-sampling container, wherein the storage tray is designed to hold the urine-sampling container.

14. The urinary catheter kit according to claim 1, further comprising step-by-step catheterization instructions imprinted on the working tray.

15. The urinary catheter kit according to claim 14, further comprising an instruction to not separate the working tray from the storage tray imprinted on the working tray.

16. The urinary catheter kit according to claim 1, wherein the storage tray comprises paperboard.

17. The urinary catheter kit according to claim 16, wherein the working tray is nested on the storage tray by inserting folded-over longitudinal edges or tabs of the storage tray in a gap between longitudinal sides and an overhang of the working tray, the gap including protrusions configured to engage the folded-over longitudinal edges or tabs of the storage tray and fasten together the working tray and the storage tray.

18. The urinary catheter kit according to claim 1, wherein the urinary catheter is a Foley catheter, and wherein the drainage receptacle comprises a urine meter.

19. The urinary catheter kit according to claim 1, further comprising an outer packaging encompassing the working tray, the storage tray, and the plurality of urinary catheter components.

20. The urinary catheter kit according to claim 19, wherein the urinary catheter kit further comprises a peri-care kit positioned between the working tray and the outer packaging of the urinary catheter kit.

* * * * *